(12) United States Patent
Kuo et al.

(10) Patent No.: US 10,577,322 B2
(45) Date of Patent: Mar. 3, 2020

(54) 5-METHOXYTRYPTOPHAN AND ITS DERIVATIVES AND USES THEREOF

(71) Applicant: National Health Research Institutes, Miaoli County (TW)

(72) Inventors: Cheng-Chin Kuo, Miaoli County (TW); Kenneth Kun-Yu Wu, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 0 days.

(21) Appl. No.: 16/166,416

(22) Filed: Oct. 22, 2018

(65) Prior Publication Data

US 2019/0092725 A1 Mar. 28, 2019

Related U.S. Application Data

(62) Division of application No. 15/543,001, filed as application No. PCT/US2016/013131 on Jan. 13, 2016, now abandoned.

(60) Provisional application No. 62/102,675, filed on Jan. 13, 2015.

(51) Int. Cl.
*A61K 31/405* (2006.01)
*C07D 209/20* (2006.01)

(52) U.S. Cl.
CPC .......... *C07D 209/20* (2013.01); *A61K 31/405* (2013.01)

(58) Field of Classification Search
CPC ..................... C07D 209/20; A61K 31/405
See application file for complete search history.

(56) References Cited

U.S. PATENT DOCUMENTS

| 4,448,785 A | 5/1984 | Kathawala et al. |
| 7,855,215 B2 | 12/2010 | Bold et al. |
| 8,288,549 B2 | 10/2012 | Henrich et al. |
| 2006/0160884 A1 | 7/2006 | Park et al. |
| 2012/0329846 A1 | 12/2012 | Matsumoto et al. |
| 2018/0009750 A1 | 1/2018 | Kuo et al. |

FOREIGN PATENT DOCUMENTS

| DE | 19814546 A | 10/1999 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Hi no, et al. Document No. 92:58535 retrieved from STN; entered in STN on May 12, 1984.
Kost, et al. Document No. 66: 18837 retrieved from STN; entered in STN on May 12, 1984.
Sagitullin, et al. Document No. 61: 18120 retrieved from STN; entered in STN on Apr. 22, 2001.
Behforouz, etal. Document No. 127:149043 retrieved from STN; entered in STN on Apr. 6, 1997.
Somei, et al. Document No. 120:31170 retrieved from STN; entered in STN on Jan. 22, 1994.
Quiclet-Sire, et al. Document No. 137:352807 retrieved from STN; entered in STN on Jul. 28, 2002.
Hikawa, et al. Document No. 155:123664 retrieved from STN; entered in STN on May 19, 2011.
Synder, et al. Document No. 154:589134 retrieved from STN; entered in STN on May 12, 2011.
Huei-Hsuan Cheng ,Kai-Hsuan Wang ,Ling-Yun Chu,Tzu-Ching Chang,Cheng-Chin Kuo,Kenneth K. Wu, Quiescent and Proliferative Fibroblasts Exhibit Differential p300 HAT Activation through Control of 5-Methoxytryptophan Production, plos one, Feb. 11, 2014, vol. 9.
Huei-Hsuan Cheng , Cheng-Chin Kuo, Jiann-Long Yan, Hua-Ling Chen, Wei-Chung Lin, Kai-Hsuan Wang, Kelvin K.-C. Tsai, Hayrettin Guvén, Emilie Flaberg, Laszlo Szekely, George Klein, and Control of cyclooxygenase-2 expression and tumorigenesis by endogenous 5-methoxytryptophan., Proc Natl Acad Sci, Aug. 14, 2012, vol. 109.
Kenneth K Wu, Huei-Hsuan Cheng and Tzu-Ching Chang, 5-methoxyindole metabolites of L-tryptophan: control of COX-2 expression, inflammation and tumorigenesis., J Biomed Sci. 2014.
Chien-Chin Cheng, 5-Methoxytryptophan Plays Critical Role in Suppressing LPS/TLR4-Mediating Inflammatory Response (2014).
María De La Luz Velázquez-Monroy, Miguel Angel Ordorica-Vargas, Juan Guillermo Ordorica-Vargas & Pedro Alberto Lehmann Feitler, Modelling the Effect of Physicochemical Properties on the Antihypertensive Activity ofTryptophan Positional Analogs, Using Artificial Neural Networks, Proc. West. Pharmacol. Soc. 41: 161-165 (1998).
Jian-Guo Tang ,Han Liu,Zhong-Yu Zhou and Ji-Kai Liu, Facile and Efficient One-Pot Synthesis of β-Carbolines, Synthetic Communications, vol. 40, 2010—Issue 10,pp. 1411-1417.
Georg Blaser,John M.Sanderson,Andrei S.Batsanov,Judith A.K. Howard, The facile synthesis of a series of tryptophan derivatives, Tetrahedron Letters, vol. 49, Issue 17, Apr. 21, 2008, pp. 2795-2798.
Shuo Zhao, Xuebin Liao, and James M. Cook, Enantiospecific, Stereospecific Total Synthesis of (+)-Majvinine, (+)-10-Methoxyaffinisine, and (+)-Na-Methylsarpagine as Well as the Total Synthesis of the Alstonia Bisindole MacralstonidineK, Org. Lett., 2002, 4 (5), pp. 687-690.

(Continued)

*Primary Examiner* — Shawquia Jackson
(74) *Attorney, Agent, or Firm* — Bacon & Thomas, PLLC

(57) ABSTRACT

A 5-methoxytryptophan and its derivatives are disclosed, wherein the 5-methoxytryptophan and its derivatives are represented by the following formula (I):

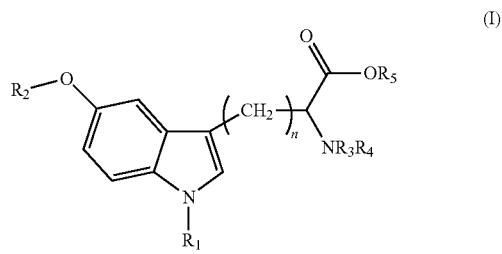

wherein $R_1$, $R_2$, $R_3$, $R_4$, $R_5$, and n are defined in the specification. In addition, the present invention also provides novel uses of the 5-methoxytryptophan and its derivatives for treating inflammatory-related disease and cancers.

2 Claims, 40 Drawing Sheets

(56) References Cited

OTHER PUBLICATIONS

Hidemasa Hikawa and Yuusaku Yokoyama, Palladium-Catalyzed Mono-N-allylation of Unprotected Anthranilic Acids with Allylic Alcohols in Aqueous Media, J. Org. Chem., 2011, 76 (20), pp. 8433-8439.
Mohammad Behforouz, Wen Cai, Farahnaz Mohammadi, Mark G. Stocksdale,Zhengxiang Gu, Mohammad Ahmadian, Darric E. Baty, Michele R. Etling,Charmaine H. Al-Anzi, Tyson M. Swiftney, Lee R. Tanzer, Ronald R. Merriman, and Nancy C. Behforouz, Synthesis and Evaluation of Antitumor Activity of Novel N-Acyl-lavendamycin Analogues and Quinoline -5,8-diones, Bioorg Med Chem. Jan. 1, 2007; 15(1): 495-510.
Park, K., Gopalsamy, A., Aplasca, A., Ellingboe, J.W., Xu, W., Zhang, Y., Levin, J.I., Synthesis and activity of tryptophan sulfonamide derivatives as novel non-hydroxamate TNF-alpha converting enzyme (TACE) inhibitors,(2009) Bioorg.Med.Chem. 17: 3857-3865.
Elena Angelini, Cesarino Balsamini, Francesca Bartoccini, Simone Lucarini and Giovanni Jiersanti, Switchable Reactivity of Acylated α, β-Dehydroamino Ester in the Friedel-Crafts Alkylation of Indoles by changing the Lewis Acid, J. Org. Chem., 2008, 73 (14), pp. 5654-5657.
A.N.Kostt.V.Koronellir.S.Sagitullin V.A.Puchkovyu.V.Denisovn.S. Wulfson, The formation of Deptidoketones from N-methylamino acids, Tetrahedron, vol. 25, Issue 15, 1969, pp. 3067-3074.
Kunihiko Irie, Akihiko Ishida, Tohru Nakamura, Tokuro Ohishi, Syntheses of Substituted L- and D-Tryptophans, Chemical and Pharmaceutical Bulletin,1984 vol. 32 Issue 6 pp. 2126-2139.

* cited by examiner

5-METHOXYTRYPTOPHAN AND ITS DERIVATIVES AND USES THEREOF

CROSS REFERENCE TO RELATED APPLICATION

This application is a division of U.S. patent application for "5-methoxytryptophan and its derivatives and uses thereof", U.S. application Ser. No. 15/543,001 filed Jul. 12, 2017, and the subject matter of which is incorporated herein by reference.

BACKGROUND OF THE INVENTION

1. Field of the Invention

The present invention relates to 5-methoxytryptophan and its derivatives and uses thereof. More specifically, the present invention relates to novel 5-methoxytryptophan and its derivatives and uses thereof for treating inflammatory-related diseases and cancers.

2. Description of Related Art

Abnormal activation of innate immune system has been implicated in the development of inflammatory disorders such as septic shock, multiple organ failure and atherosclerosis. Toll-like receptors (TLRs) play a critical role in regulating immune response and maintaining immune homeostasis. Inappropriate activation of TLR signaling by pathogen components and endogenous harmful molecules is a major contributor to systemic inflammation such as sepsis. There is growing evidence that TLRs play a key role in mediating systemic responses to invading pathogens during systemic inflammation and sepsis. In particular, activation of TLR4 by LPS is thought to be an important trigger of inflammatory response in sepsis. In addition to LPS, TLR4 can also be activated by endogenous molecules such as high mobility group box 1 (HMGB1) as a late mediator of lethal sepsis, which in turn initiates a secondary immunostimulatory cascade. Systemic inflammatory response syndrome is induced most commonly by a systemic infection of gram-negative bacteria and the subsequent release of LPS, which activates TLR4 signaling. The excessive stimulation of the host immune system by LPS results in high levels of inflammatory cytokines in the circulation and disseminated intravascular coagulation.

Systemic inflammation is characterized by metabolic syndrome, cardiovascular decompensation, multiple organ failure, disseminated intravascular coagulation and shock. These clinical manifestations are attributed to inappropriate or extensive inflammatory responses to uncontained bacterial infection and the endotoxins produced by gram-negative bacteria notably lipopolysaccharide (LPS). Excessive immune responses lead to production of very high levels of proinflammatory cytokines (cytokine storm) and overexpression of proinflammatory mediators such as cyclooxygenese-2 (COX-2) and inducible nitric oxide synthase (iNOS). Treatment of systemic inflammatory response syndrome is limited to fluid administration, oxygen supplement, antibiotics and other supportive measures. Specific therapeutic approaches targeting proinflammatory cytokines, coagulation cascade, LPS or immune responses are unsuccessful or have marginal efficacy.

Abnormal activation of the innate immune system and the resulting chronic inflammation have been implicated in the development and progression of chronic and metabolic diseases including atherosclerosis (Hansson G K & Hermansson A. The immune system in atherosclerosis. *Nat Immunol* 12:204-212 (2011)). Considerable evidence suggests that infectious agents could contribute to cardiovascular diseases. Vascular injury are often caused by uncontrolled infection with releases of endotoxins notably LPS. LPS activates toll-like receptor 4 (TLR4) which transmits signals to activate NF- B and C/EBP resulting in excessive production of proinflammatory mediators thereby inducing endothelial and vascular damages. In addition to LPS, TLR4 can also be activated by endogenous molecules such as high mobility group box 1 (HMGB1) as a late mediator of inflammation, which contributes to the development of atherosclerosis. ApoE-knockout mouse challenged with *Porphyromonas gingivalis* not only accelerates atherosclerosis but also increases expression of TLR2 and TLR4. Vascular disease is recognized as an inflammatory disease—inflammation activates endothelium and the underlying medial VSMCs (Hansson G K. Inflammation, atherosclerosis, and coronary artery disease. *N Engl J Med* 352, 1685-95 (2005)). The pathogenic VSMC migration and proliferation (leading to arteriosclerosis) are somewhat similar to that of systemic inflammation as well as cancer cell growth and invasion. We hypothesized that 5-MTP might protect against vascular injury-induced inflammation and the subsequent endothelial dysfunction and VSMC proliferation and migration, and consequent neointima formation.

Therefore, it is desirable to provide a new therapeutic agents and methods to conquer the aforementioned serious human illness.

SUMMARY OF THE INVENTION

This invention is based on the discovery that certain 5-methoxytryptophan and its derivatives can be used as anti-inflammatory diseases and anti-cancer agents. Thus, the object of the present invention is to provide 5-methoxytryptophan and its derivatives and methods for treating an inflammatory-related disease and cancers with the same.

One aspect of the present invention is related to a compound of formula (I):

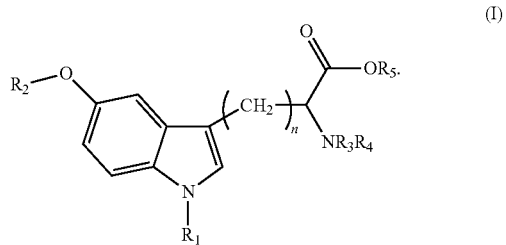

In this formula, $R_1$ is halogen atom, $C_1$-$C_{10}$ alkyl, $C_2$-$C_{10}$ alkenyl, $C_2$-$C_{10}$ alkynyl, $C_3$-$C_{20}$ cycloalkyl, or $C_3$-$C_{20}$ cycloalkenyl; $R_2$ is $C_1$-$C_{10}$ alkyl, $C_2$-$C_{10}$ alkenyl, $C_2$-$C_{10}$ alkynyl, $C_3$-$C_{20}$ cycloalkyl, or $C_3$-$C_{20}$ cycloalkenyl; $R_3$ is H, $C_1$-$C_{10}$ alkyl, $C_2$-$C_{10}$ alkenyl, $C_2$-$C_{10}$ alkynyl, $C_3$-$C_{20}$ cycloalkyl, or $C_3$-$C_{20}$ cycloalkenyl; $R_4$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C(O)R_a$, or $C(O)OR_a$; in which $R_a$ is H, $C_1$-$C_{10}$ alkyl, $C_3$-$C_{20}$ cycloalkyl, $C_3$-$C_{20}$ heterocycloalkyl, aryl, or heteroaryl; $R_5$ is H, $C_1$-$C_{10}$ alkyl, $C_3$-$C_{20}$ cycloalkyl, $C_3$-$C_{20}$ heterocycloalkyl, aryl, or heteroaryl; and n is 0-5.

One subset of the just-described compounds includes 5-methoxytryptophan and its derivatives, in which each $R_1$ and $R_2$, independently; is H or $C_1$-$C_{10}$ alkyl. In these compounds, preferably, $R_1$ is H, and $R_2$ is $C_1$-$C_3$ alkyl.

Another subset of the just-described compounds includes 5-methoxytryptophan and its derivatives, in which $R_3$ is H, $C_1$-$C_{10}$ alkyl, and $R_4$ is H, $C_1$-$C_{10}$ alkyl, $C(O)R_a$, or $C(O)OR_a$, in which $R_a$ is H, or $C_1$-$C_{10}$ alkyl. In these compounds, preferably, $R_3$ is H, and $R_4$ is H or $C(O)R_a$, in which $R_a$ is $C_1$-$C_3$ alkyl.

Another subset of the just-described compounds includes 5-methoxytryptophan and its derivatives, in which $R_5$ is H or $C_1$-$C_{10}$ alkyl. In these compounds, preferably, $R_5$ is H or $C_1$-$C_3$ alkyl.

A further subset of the just-described compounds includes 5-methoxytryptophan and its derivatives, in which n is 1 or 2.

The term "alkyl" refers to a saturated, linear or branched hydrocarbon moiety, such as —$CH_3$ or —$CH(CH_3)_2$. Examples of alkyl include, but are not limited to, methyl, ethyl, n-propyl, i-propyl, n-butyl, i-butyl, and t-butyl. The term "alkenyl" refers to a linear or branched hydrocarbon moiety that contains at least one double bond, such as —CH=CH—$CH_3$. Examples of alkenyl include, but are not limited to, ethenyl, propenyl, propenylene, allyl, and 1,4-butadienyl. The term "alkynyl" refers to a linear or branched hydrocarbon moiety that contains at least one triple bond, such as —C≡C—$CH_3$. Examples of alkynyl include, but are not limited to, ethynyl, ethynylene, 1-propynyl, 1- and 2-butynyl, and 1-methyl-2-butynyl. The term "cycloalkyl" refers to a saturated, cyclic hydrocarbon moiety. Examples of cycloalkyl include, but are not limited to, cyclopropyl, cyclobutyl, cyclopentyl, cyclopentenyl, cyclohexyl, cyclohexenyl, cycloheptyl, and cyclooctyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S). Examples of heterocycloalkyl groups include, but are not limited to, piperazinyl, pyrrolidinyl, dioxanyl, morpholinyl, and tetrahydrofuranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pynolyl, thienyl, oxazolyl, imidazolyl, thiazolyl, pyridyl, pyrimidinyl, quinazolinyl, quinolyl, isoquinolyl and indolyl. The term "halogen atom" refers to F, Cl, Br or I.

Alkyl, alkenyl, alkynyl, cycloalkyl, cycloalkenyl, heterocycloalkyl, aryl, and heteroaryl mentioned herein include both substituted and unsubstituted moieties, unless specified otherwise. Possible substituents on cycloalkyl, cycloalkenyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The compounds described above include the compounds themselves, as well as their salts, their solvates, and their prodrugs, if applicable. A salt, for example, can be formed between an anion and a positively charged group (e.g., amino) on 5-methoxytryptophan and its derivatives. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on 5-methoxytryptophan and its derivatives. Suitable cations include sodium ion, potassium ion, magnesium ion, calcium ion, and an ammonium cation such as tetramethylammonium ion. The compounds also include those salts containing quaternary nitrogen atoms. Examples of prodrugs include esters and other pharmaceutically acceptable derivatives, which, upon administration to a subject, are capable of providing active compounds as described above. A solvate refers to a complex formed between an active 5-methoxytryptophan or its derivative and a pharmaceutically acceptable solvent. Examples of pharmaceutically acceptable solvents include water, ethanol, isopropanol, ethyl acetate, acetic acid, and ethanolamine.

One subset of the just-described compounds includes 5-methoxytryptophan derivatives, with the proviso that $R_1$, $R_3$, $R_4$ and $R_5$ are not H when $R_2$ is $C_1$-$C_{10}$ alkyl.

In another aspect, this invention features a method for treating an inflammatory-related disease. The method includes administering to a subject in need thereof and effective amount of one or more compounds of formula (I) shown above. Examples of inflammatory-related diseases include sepsis, Systemic Lupus Erythematosus (SLE), cardiovascular diseases, metabolic syndrome, cancer, septicemia and diverse inflammatory joint, gastrointestinal, and renal diseases.

In further another aspect, this invention also features a method for treating a cancer. The method includes administering to a subject in need thereof and effective amount of one or more compounds of formula (I) shown above. Cancer that can be treated by the method of this invention includes both solid and haematological tumours of various organs. Examples of solid tumors include pancreatic cancer, bladder cancer (e.g., urothelium cancer), colorectal cancer, breast cancer (e.g., metastatic breast cancer), male genital tract cancer (e.g., seminal vesicle cancer, testes cancer, germ cell tumors, and prostate cancer such as androgen-dependent and androgen-independent prostate cancer), renal cancer (e.g., metastatic renal cell carcinoma), hepatocellular cancer, lung cancer (e.g., small cell lung cancer, non-small cell lung cancer, bronchioloalveolar carcinoma, and adenocarcinoma of the lung), ovarian cancer (e.g., progressive epithelial or primary peritoneal cancer), cervical cancer, uterus cancer, gestational trophoblastic disease (e.g., choriocarcinoma), gastric cancer, bile duct cancer, gallbladder cancer, small intestine cancer, esophageal cancer, oropharyngeal cancer, hypopharyngeal cancer, eye cancer (e.g., retinoblastoma), nerve cancer (e.g., Schwannoma, meningioma, neuroblastoma, and neuroma), head and neck cancer (e.g., squamous cell carcinoma of the head and neck), melanoma, plasmacytoma, endocrine gland neoplasm (e.g., pituitary adenoma, thyroid cancer, and adrenal tumor), neuroendocrine cancer (e.g., metastatic neuroendocrine tumors), brain tumors (e.g., glioma, anaplastic oligodendroglioma, glioblastoma multiforme, and astrocytoma such as adult anaplastic astrocytoma), bone cancer, and sarcomas from soft tissue or bone (e.g., Kaposi's sarcoma). Examples of hematologic malignancy include acute myeloid leukemia, chloroma, chronic myelogenous leukemia or CML (e.g., accelerated CML and CML blast phase), acute lymphoblastic leukemia, chronic lymphocytic leukemia, Hodgkin's disease, non-Hodgkin's lymphoma (e.g., follicular lymphoma, cutaneous T-cell lymphoma such as mycosis fungoides, and mantle cell lymphoma), B-cell lymphoma, multiple myeloma, Waldenstrom's macroglobulinemia, myelodysplastic syndromes (e.g., refractory anemia, refractory anemia with ringed siderblasts, refractory anemia with excess blasts or RAEB, and RAEB in transformation or RAEB-T, and myeloproliferative syndromes).

The term "treating" or refers to administering one or more 5-methoxytryptophan and its derivatives to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

The term "an effective amount" refers to the amount of a 5-methoxytryptophan or its derivative that is required to confer a therapeutic effect on the treated subject. Effective amounts may vary, as recognized by those skilled in the art, depending on the types of diseases treated, route of administration, excipient usage, and the possibility of co-usage with other agents.

Also within the scope of this invention is a pharmaceutical composition containing one or more 5-methoxytryptophan and its derivatives described above for use in treating one of the above-described diseases and cancers, and the use of such a composition for the manufacture of a medicament for this treatment.

Shown below are exemplary 5-methoxytryptophan and its derivatives of the present invention:

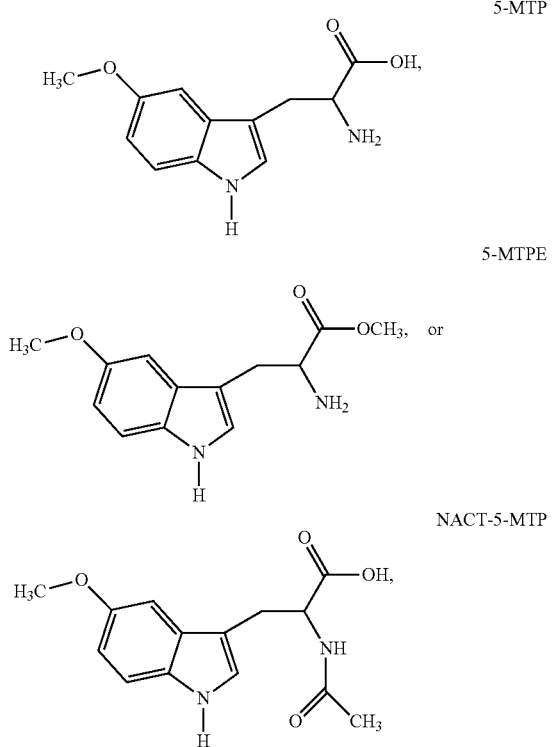

wherein 5-MTP refers to 5-methoxytryptophan; 5-MTPE refers to ester-5-MTP; and. NACT-5MTP refers to N-acetyl-5-MTP.

Other objects, advantages, and novel features of the invention will become more apparent from the following detailed description when taken in conjunction with the accompanying drawings.

DETAILED DESCRIPTION OF THE PREFERRED EMBODIMENT

Synthesis of 5-MTP and its Derivatives

Figure 1A:
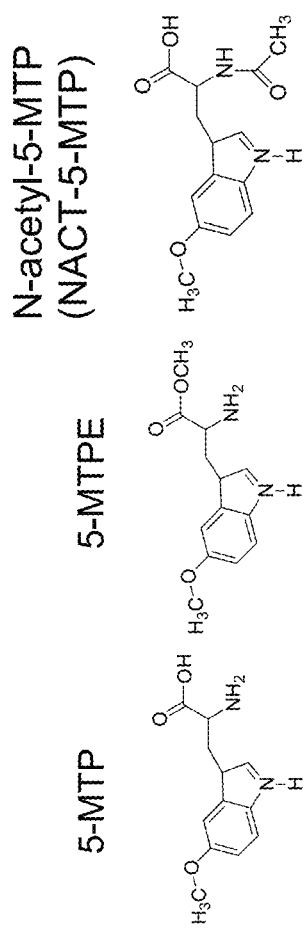
FIG. 1A shows structures of 5-MTP and its derivatives of the present invention.
Figure 1B:
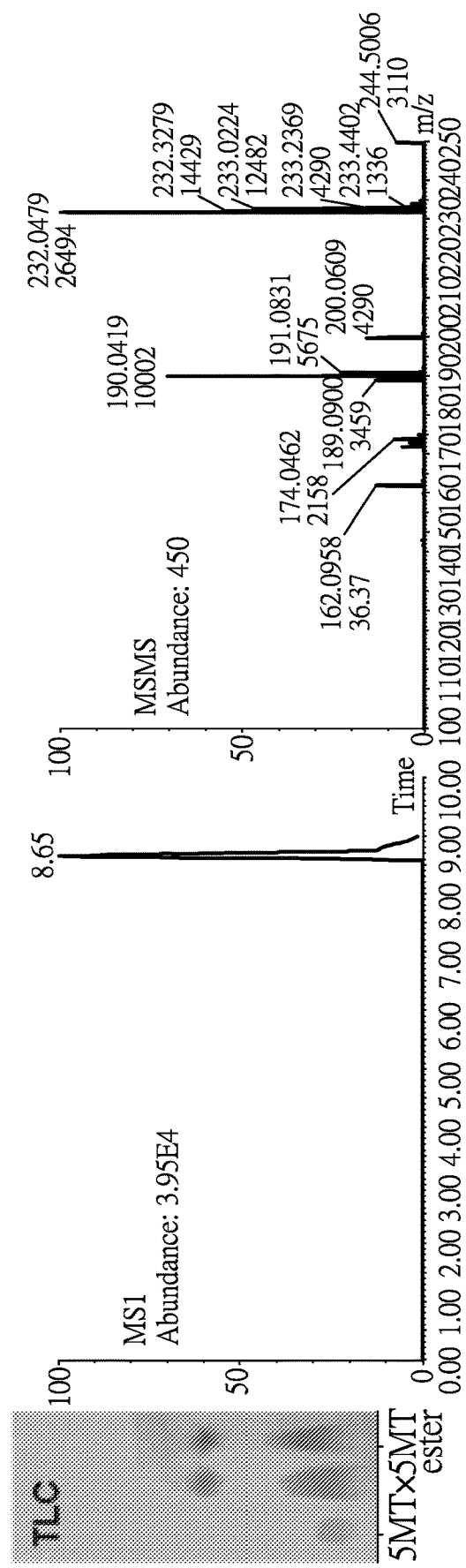
FIG. 1B shows thin layer chromatography and mass spectra of 5-MTPE.
Figure 1C:
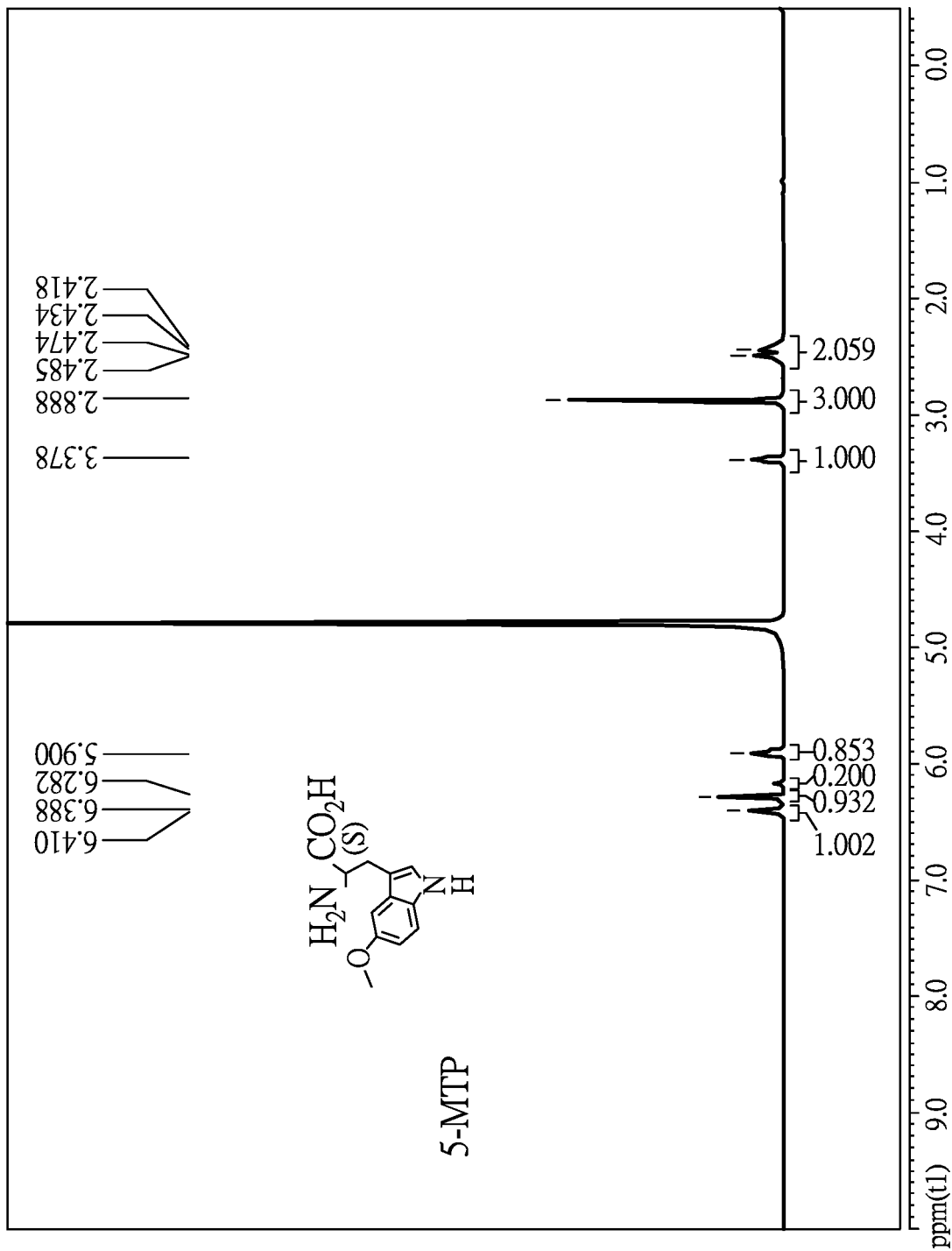
FIGS. 1C-1E show HNMR spectra of 5-MTP and its derivatives (5-MTPE and NACT-5MTP).
Figure 1D:
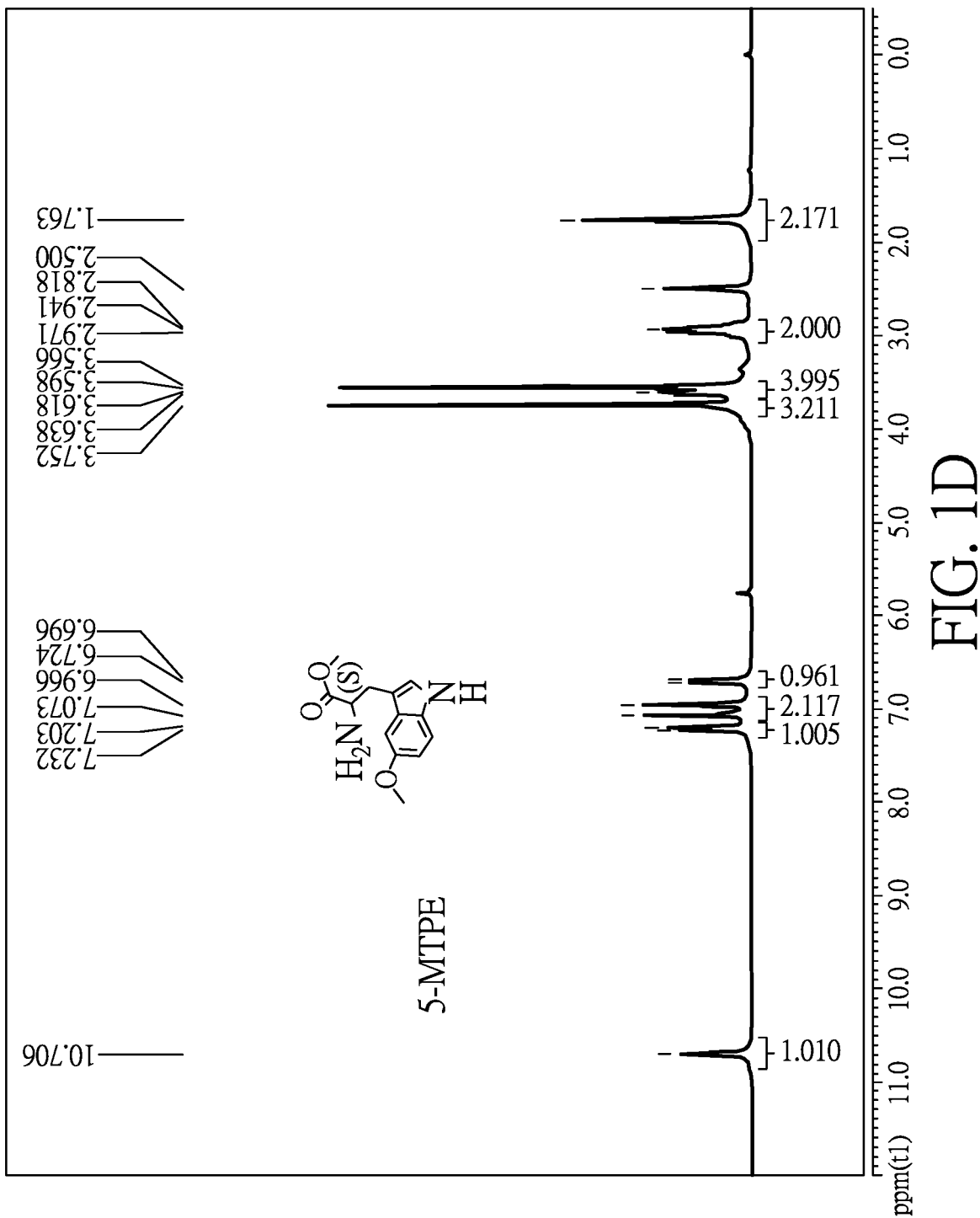
Figure 1E:
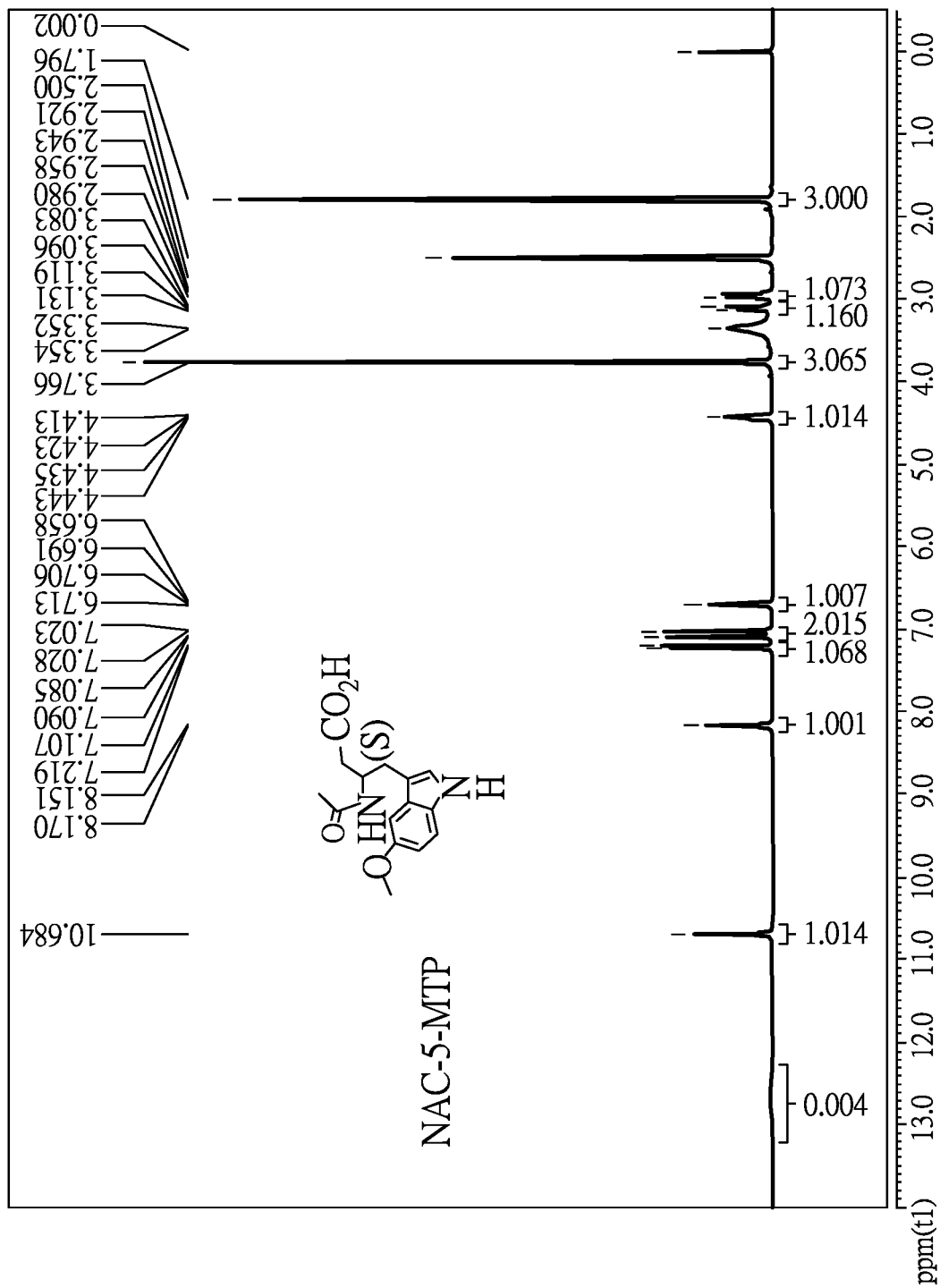

Synthesized 5-MTP provided by ASTATECH (PA, USA) was acted as material for 5-MTP derivatives synthesis as shown in synthetic scheme; and the structures of 5-MTP and its derivatives are shown in FIG. 1A.

Synthetic Scheme

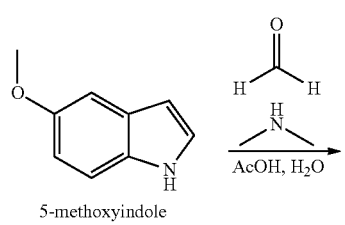

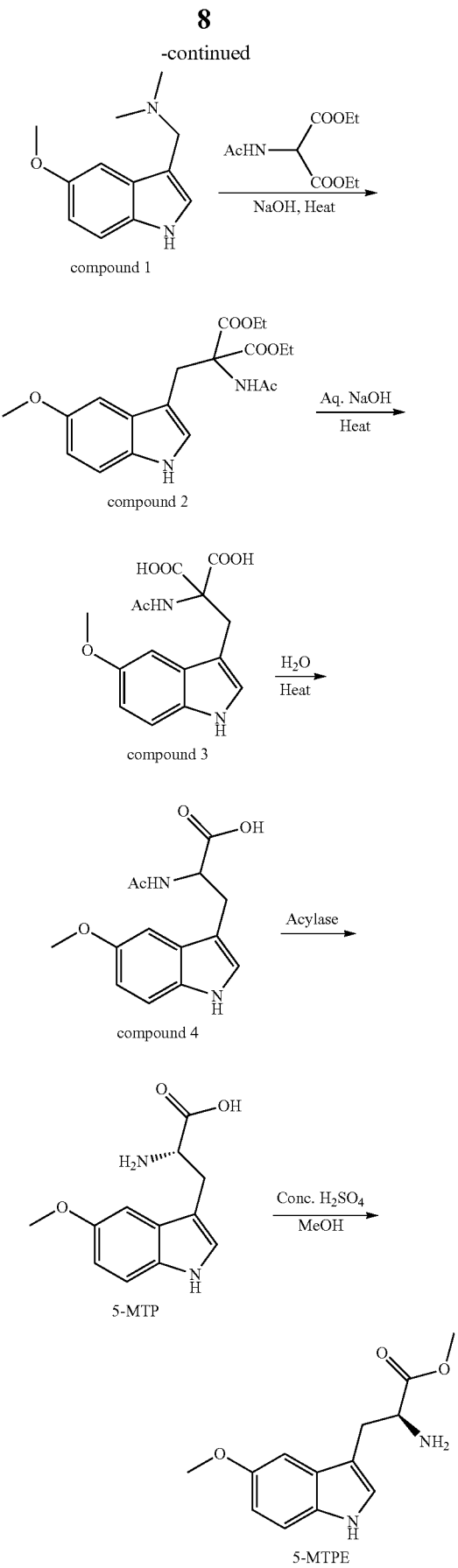

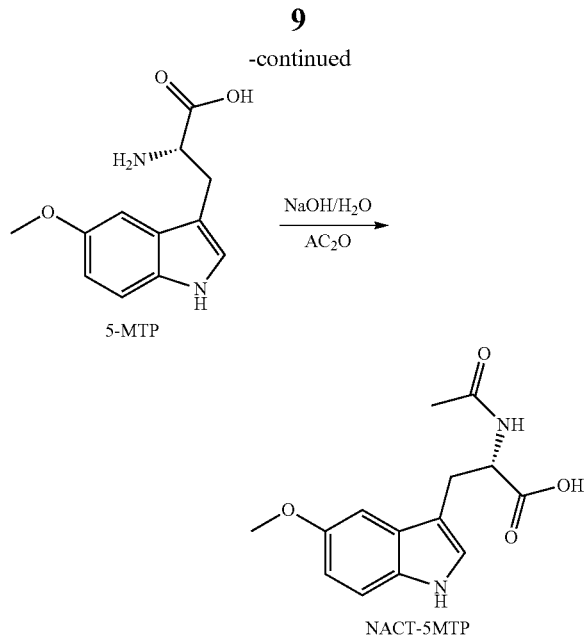

-continued

5-MTP

NACT-5MTP

Experimental Procedures:

Synthetic Step 1:

At 10° C., 33% Aq. Dimethylamine was carefully added dropwise to AcOH, and while controlled the inner temperature below 20° C., 40% Aq. Formaldehyde was added slowly.

To above solution at 10° C., 5-methoxyindole was added portionwise, and stirred under 30° C. overnight. TLC showed the starting material 5-methoxyindole was consumed. At 10° C., adjusted to pH>9 with 1N NaOH aq., extracted with MTBE five times, combined organic phases was washed with brine, dried over Na2SO4, concentrated to afford a red oil, washed with Petroleum ether got an off-white solid Compound 1 (250.0 g, yield: 75.2%).

Synthetic Step 2:

Compound 1 and 2-acetylaminomalonic acid diethyl ester were dissolved in toluene, solid NaOH was then added, and heated reflux for 18 h. TLC checked. Cooled to 10° C. while stirring, and stood for 2 h. Collected the precipitate by filtration, dried to afford a white solid Compound 2 (180.0 g, yield 98%).

Synthetic Step 3:

Compound 2 in 2N NaOH were heated to reflux for 3 h, TLC checked. Cooled to R.T., acidified to pH=2, extracted with EA for five times, combined organic phases was washed with brine, dried over $Na_2SO_4$, concentrated to afford a white solid Compound 3 (150.0 g, Yield: 100%).

Synthetic Step 4:

Compound 3 in water was heated reflux for 3 hrs, TLC checked. Cooled to R.T., Collected the precipitate by filtration, dried to afford a white solid Compound 4 (98.0 g, yield 76%).

Synthetic Step 5 (Synthesis of 5-MTP):

Compound 4 was added to a solution $KH_2PO_4$ (50 mM) in water, KOH was added stirred for 10 min., got a clean solution. $CoCl_2$ (50 mM) was added, keep pH=8, used KOH (2N aq), Acylase was added and 35-40° C. reacted for 16 hrs, TLC checked. The precipitate was collected by filtration, washed with water until the Purification of EE % above 98%, dried to afford 5-MTP (14.0 g product. Yield, 33%).

Synthetic Step 6 (Synthesis of 5-MTPE):

5-MTP was dissolved in MeOH with catalytic amount of $Conc.H_2SO_4$, the solution was then heated reflux for 24 hrs, TLC checked. The MeOH was concentrated and the residue was poured in water and basified to ph=7.5 with $NaHCO_3$, extracted with DCM for three times, combined organic phases washed with brine, dried over $Na_2SO_4$, concentrated to afford a red oil, crystallized in MTBE to afford brown solid 4.8 g of 5-MTPE (Yield: 77%).

Synthetic Step 7 (Synthesis of NACT-5MTP):

1 g of the 5-MTP was dissolved in a cooled (2N) NaOH 50 mL, At 0° C. or lower, 0.5 mL $Ac_2O$ was added dropwise, inner temperature was below 0° C., then stirred in the same condition for 0.5 hrs, acidified to pH=2, The precipitate was collected by filtration, washed with water and dry 24 h at 50° C. to get 1 g NACT-5MTPE (cat#22099).

The purity and chemical structure of the obtained 5-MTPE and NACT-5MTP were determined by thin layer chromatography (TLC), LC-MSMS and photon NMR, respectively, and these results are shown in FIGS. 1B-1F.

[In Vitro and In Vivo Experiments]

Cell Culture and Treatment

Mouse RAW264.7 macrophages were from the American Type Culture Collection and cultured in DMEM containing 10% FBS. Cells were typically pre-incubated with or without 5-MTP (Sigma-Aldrich) for 30 min before LPS treatment, unless specified otherwise. The duration of LPS (100 ng/ml) treatment varied depending on the experiment.

For peritoneal macrophage isolation, C57BL/6J mice were injected intraperitoneally with 2 ml of 4% thioglycollate. Four days after injection, the peritoneal cavity was washed with 5 ml of ice-cold RPMI1640 medium, and cells from the peritoneal exudates were collected by centrifugation, and suspended in RPMI1640 medium, then seeded on 15-cm dishes and allowed to adhere for 4 h. Floating cells were washed out, and adherent cells were used as peritoneal macrophages in the experiments. The cells were incubated with or without LPS (100 ng/ml) for the indicated time before each experiment, as in the protocol for the RAW264.7 cells.

Cell Migration and Invasion Assays

Briefly, cells ($10^4$/well) were seeded on the upper chamber (6.5-mm insert, 8-μm polycarbonate membrane; Corning Inc.), which was placed in each well of a 24-well plate. The lower chamber was filled with 700 μL DMEM supplemented with 10% FBS. For assessment of in vitro invasion, cells were seeded onto the upper chamber insert coated with Matrigel (BD Biosciences) under the same conditions as the transwell migration assays. At the indicated time, nonmigrated cells that remained at the top surface of the insert were removed with a cotton swab. Cells that migrated to the lower membrane surface and cells that invaded through the matrigel gel to the underside of the membrane were fixed, stained with 0.1% crystal violet for 20 min, and counted under light microscopy. All of the assays were done in triplicate with excellent reproducibility.

Tumor Xenograft Experiment

Six-week-old male CB-17 SCID mice, purchased from BioLASCO, were housed in a daily cycle of 12-h light and 12-h darkness and pathogen-free conditions at 26° C. at the Animal Center of the National Health Research Institutes. A549-luc-C8 cells (Caliper Life Sciences), cultured in RPMI-1640 supplemented with 10% FBS, were pretreated with 100 μM 5-MTP, 100 μM 5-MTPE or vehicle for 5 h and were inoculated into the flank of mice subcutaneously (s.c.) ($5 \times 10^6$ cells/mouse). The 5-MTP-, or 5-MTPE-treated mice (n=10) were injected with 100 mg 5-MTP or 5-MTPE /kg body weight intraperitoneally twice weekly. The vehicle group (n=10) was injected with vehicle (0.033 N HCl in RPMI medium, neutralized with NaOH) twice weekly. The size of s.c. tumors were caliper-measured twice weekly. The tumor volume was calculated according to the formula of length×width×width/2. The tumor growth was also monitored weekly by an IVIS spectrum imaging system. Mice were euthanized at day 52. Subcutaneous tumors and lungs were removed and fixed with 10% Formalin. Nodules on each lobe of the lungs were counted. Histology of the nodules was examined under microscopy by tissue section and H&E staining. The animals' care was in accordance with institutional guidelines and the protocol of in vivo experiments was approved by the Institutional Animal Care and Utilization Committee of the National Health Research Institutes.

Induction of Endotoxemia in a Mouse Model

C57BL/6 mice (6-8 wks old) were treated intraperitoneally with saline or with different concentrations of 5-MTP (23.4 or 100 mg/kg) for 30 min before intraperitoneal administration of LPS (60 mg/kg). Animals were monitored for survival and other clinical signs including ruffled fur, lethargy, diarrhea, and body weight loss. Some animals were sacrificed at different times after LPS injection. Blood samples, peritoneal exudates, lungs, and spleens were collected. All mouse experiments were approved by the institutional Animal Care and Use Committee, National Health Research Institutes.

Cytokine-specific ELISA

Cytokine levels in the culture supernatants and serum were determined in microtiter plates (96-well) by a specific sandwich ELISA (Biosource) as previously described (Wu, J. Y. & Kuo, C. C. Pivotal role of ADP-ribosylation factor 6 in Toll-like receptor 9-mediated immune signaling. *J Biol Chem* 287, 4323-4334 (2012)) (Lee, G. L., et al. TLR 2 induces vascular smooth muscle cell migration through cAMP response element-binding protein-mediated interleukin-6 production. *Arterioscler Thromb Vasc Biol* 32, 2751-2760 (2012); hereinafter, Lee, G. L., et al.).

Western Blot Analysis

Cellular protein were resolved by 5% to 20% SDS-PAGE and transferred to nitrocellulose membranes and blotted with specific antibodies as previously described (Lee, G. L., et al.).

Promoter-luciferase Reporter Assay

RAW264.7 macrophages were cotransfected with COX-2 promoter-luciferase, IL-6 promoter-luciferase constructs as previously described (Lee, G. L., et al.) or p5xNF-κB-luciferase (Stratagene) and pcDNA3.1-β-galactosidase plasmids using FuGENE 6 (Roche). After overnight transfection, the cells were incubated with or without LPS in the presence or absence of 5-MTP for 8 h. After treatment, cells were lysed, and luciferase activity was measured using an assay kit (Promega). β-galactosidase activity was used to normalize the data.

MPO Activity Assay

Myeloperoxidase (MPO) activity of lung tissue was assayed by Myeloperoxidase fluorometric detection kit (Enzo Life Sciences). In brief, lung tissue specimens were homogenized by Tissuelyser II (Qiagen) in tissue protein extraction buffer (pH 7.4 25 mM Tris buffer, 150 mM NaCl, 0.5% sodium deoxycholate, 2% NP-40 and 0.2% SDS), and centrifuged at 12,000×g for 20 mM at 4° C. The supernatants were removed and the pellets were homogenized by Tissuelyser II for 30 seconds in 1 ml assay buffer with 0.5% hexadecyltrimethylammonium, and then samples were frozen, thawed three times, andcentrifuged at 8,000×g for 20 min. Collected supernatants and standard were mixed with reaction cocktail (50 μM detection reagent and 20 μM hydrogen peroxide in 1X assay buffer at room temperature in the dark. After 30 min incubation, MPO activity was determined by measuring the fluorescence intensity at excitation 530 nm and emission at 600 nm in a fluorescent plate reader.

Caspase-3 Activity Assay

Caspase-3 activity was determined by the cleavage of the fluorometric substrate z-DEVD-AMC (Upstate Biotechnology) as previously described (Kuo, C. C., Liang, C. M., Lai, C. Y. & Liang, S. M. Involvement of heat shock protein (Hsp)90 beta but not Hsp90 alpha in antiapoptotic effect of CpG-B oligodeoxynucleotide. *J Immunol* 178, 6100-6108 (2007)).

Histology and Immunohistochemistry

For histological studies, the lungs were perfused with saline, and immersed in formalin for 24 h. Tissue blocks were placed in formalin, dehydrated in a graded series of ethanol, embedded in paraffin, cut into 3 μm-thick serial sections, and stained with haematoxylin and eosin for detecting inflammatory cells, alveolar congestion and alveolar septal wall thickness and interstitial edema.

Prior to immunohistochemical detection of COX-2, iNOS, Ly6g, or cleaved caspase-3 in lung sections, sections were deparaffinized with xylene, progressively rehydrated through graded alcohols. Antigen sites were retrieved by heating the sections on slides in pH 8 EDTA antigen. retrieval (Trilogy; Cell Marque Corporation) in electric pressure cooker for 15 min. Sections were sequentially blocked by UltraVision hydrogen peroxide block (Thermo) for 10 minutes and UltraVision protein block for additional 5 minutes. All antibodies described hereafter were diluted in blocking buffer. Sections were incubated at room temperature for 2 h with primary antibody and then washed in PBST. The sections were incubated with primary antibody amplifier quanta (Thermo) for 10 minutes. After rinsing with PBST, the sections were incubated with HRP Polymer Quanto (Thermo) for 10 minutes and washed three times with PBST. COX-2, iNOS, Ly6g and cleaved caspase-3 were visualized by the addition of DAB Quanto Chromogen: Substrate for 3 minutes. Tissues were also counterstained with hematoxylin.

Patient Enrollment and Measurement of Serum 5-MTP Levels

Forty patients with CAD (161 men and 66 women; mean age, 61.2±12.13 years) and 80 control subjects (43 men and 37 women; mean age, 40±13.34 years) without CAD and known systemic disease were enrolled in the study between September 2013 and July 2015. The Ethics Committee on Human Studies at Tri-Service General Hospital, National Defense Medical Center in Taiwan approved the study protocol (TSGHIRB#2-102-05-104 and 2-102-05-105) and written informed consent was obtained from all participants. The presence of CAD was confirmed by coronary angiography and CAD was defined as more than 50% angiographic diameter stenosis in one or more coronary arteries. Blood was drawn from patients prior to 23 angiography and serum collected and stored at −80° C. until analysis.

Lipid Accumulation and Atherosclerotic Lesion Formation in Arteries of Mice

ApoE-deficient mice at 6 weeks were placed on a Western high fat diet containing 1.25% cholesterol and 21% fat (Research. Diets). The mice were simultaneously treated with vehicle (PBS), 5-MTP or 5-MTPE (23.4 mg/kg body weight, 3 times a week) by intraperitoneal injection. After 8 weeks, the aortic trees were dissected and lesions examined in the aortic arch and its branches. The aortas were carefully freed of connective and adipose tissue under a dissection microscope, opened longitudinally and stained with Oil red 0.

Arterial Calcification in Mice

ApoE-deficient mice were fed with on a Western high fat diet containing 1.25% cholesterol and 21% fat (Research Diets) starting at 6 weeks of age. The mice were simultaneously treated with vehicle (PBS) or 5-MTP (23.4 mg/kg body weight, 3 times a week) by intraperitoneal injection. After 20 weeks, the aortic trees were dissected and lesions examined in the aortic arch and its branches. Vascular calcifications in the aortic root were evaluated by von Kossa staining.

Neointima Formation Model of Carotid Artery Ligation in Mice

Approximately 12-week-old male C57BL/6 wild-type mice ational Laboratory Animal Center, Taiwan) were subjected to a neointima formation model by ligating the left common carotid artery (LCCA). The Institutional. Animal Care and Use Committee of National Health Research Institutes, Taiwan approved all experimental procedures (#NHRI-IACUC-101144-A). Mice were anesthetized with tribromoethanol solution at a dose of 250 mg/kg by IP injection. After assessing the level of anesthesia by checking the pedal reflex, the LCCA was exposed through a midline incision in the neck. The LCCA was then ligated near the carotid bifurcation with a suture, skin closed, and the animals were allowed to recover from anesthesia and showed no symptoms of stroke. Following surgery, mice were treated with vehicle (PBS) or 100 mg/kg of 5-MTP (Sigma, M4001) by IP injection 3 times a week. 5-MTP was dissolved in 0.05 N HCl (made in PBS) first, pH adjusted to 7.4 by NaOH, and then a stock solution of 6.5 mg/mL was prepared with PBS. The stock solution was then sterilized by filtering through a 0.22 µm-filter before use. At indicated time points (4, 7, and 28 d after surgery), mice were anesthetized with tribromoethanol solution (500-750 mg/kg), perfused with saline, followed by 10% neutral-buffered-formalin. The contralateral control (right common carotid artery) and ligated LCCA were then carefully dissected, excised, and immersed in 10% formalin before processing and embedding in paraffin.

Statistical Analysis

All values were given as mean ±S.D. The statistical significance of difference between treatment and control groups was calculated with a t-test or 1-way ANOVA. P values of less than 0.05 were considered statistically significant

[Results]

5-methoxytryptophan Derivatives Control COX-2 Expression.

After pretreating A549 cells with different concentrations of 5-MTP, 5-MTPE and NACT-5-MTP for 30 min, cells were stimulated with PMA for 8 h. Cell lysates were immunoblotted with antibodies for COX-2 or β-actin. The experiments were repeated 3 times with similar results.

Figure 1F:
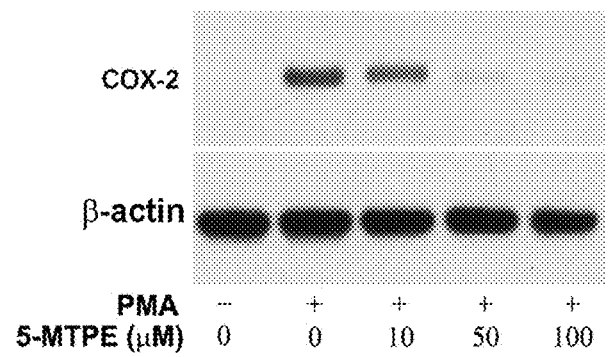
FIG. 1F shows results of suppressive activity of 5-MTP and its derivatives in PMA-induced A549 COX-2 expression.
Figure 1F:
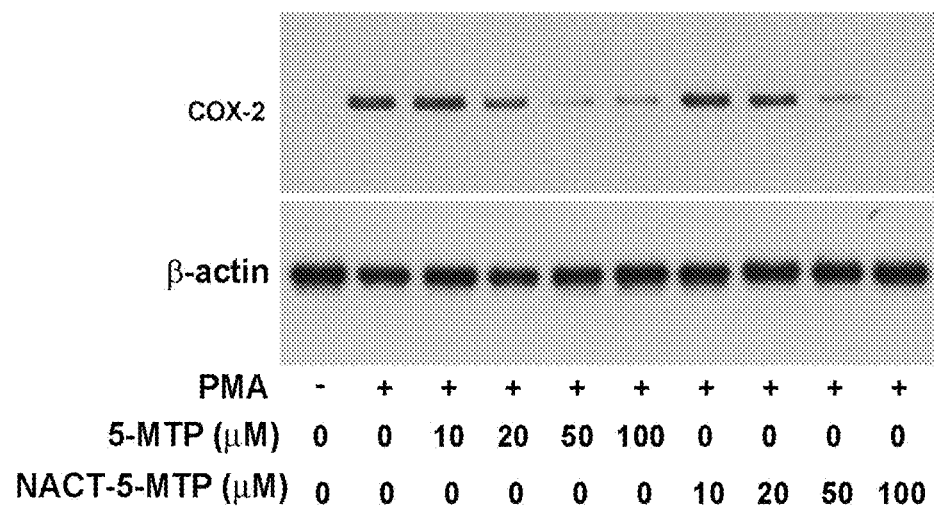

According to the result shown in FIG. 1F, as 5-MTP effect, both 5-MTPE and NACT-5MTP dose-dependently blocked PMA-induced COX-2 protein expression in A549 cells. Furthermore, the COX-2 suppressive activity of both 5-MTP derivatives is potent than that of 5-MTP.

As serotonin, 5-methoxytryptamine and tryptophan share an indole backbone with 5-MTP, we determined the effect of these compounds on PMA-induced COX-2 expressions in A549 cells. As shown in the following Table 1, neither serotonin nor 5-methoxytryptamine or tryptophan exerted an effect on COX-2 expression levels, suggesting that the 5-methoxy-indole-3-propionic acid moiety is required for inhibiting PMA-induced COX-2 expression. Collectively, these results demonstrated that 5-MTP and its derivatives suppress PMA-induced COX-2 expression in A549 lung cancer cells.

TABLE 1

| Suppressive activity in PMA-induced A549 COX-2 expression | |
|---|---|
| Tryptophan | − |
| Serotonin | − |
| 5-methoxytryptamine | − |
| 5-MTP | + |
| 5-MTPE | + |

5-Methoxytryptophan Derivatives Block Cancer Migration and Tumor Growth.

Lung cancer A549 and breast cancers BT474 and T47D cells were pretreated with different concentrations of 5-MTP or 5-MTPE for 30 min, then stimulated with PMA for 4 h or 24 h. Cell migration was measured by the transwell migration assay. The results show that 5-MTP, 5-MTPE and NACT-5MTP abrogated A549 (FIG. 2A) and breast cancer BT474 and T47D (FIG. 2B) cell migration induced by PMA for 4 h or 24 h.

In addition, A549 ($5 \times 10^6$ cells) was injected subcutaneously into the flank of SCID-Beige mice. 10 mice each received intraperitoneal injection of 5-MTP (100 mg/kg), 5-MTPE (100 mg/kg) or vehicle twice weekly. Caliper measurement of the subcutaneous tumor volume periodically for 7 weeks. The result shown in FIG. 2C indicates that 5-MTP and 5-MTPE suppressed tumor volume in a time-dependent manner. The average tumor volume at 7-week in the 5-MTP treated group was ~50% of that in the control group.

Figure 2A:
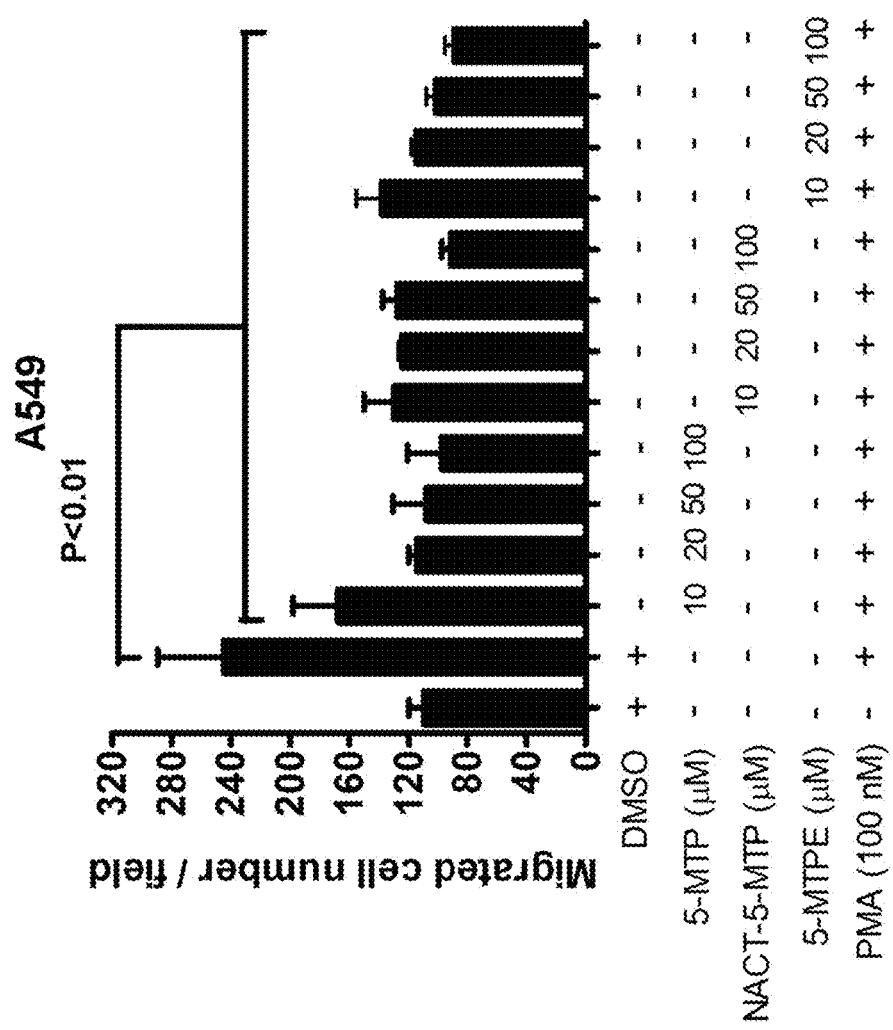
FIG. 2A shows results of cell migration assays in A549 lung cancer cells by treating 5-MTP or 5-MTPE.
Figure 2B:
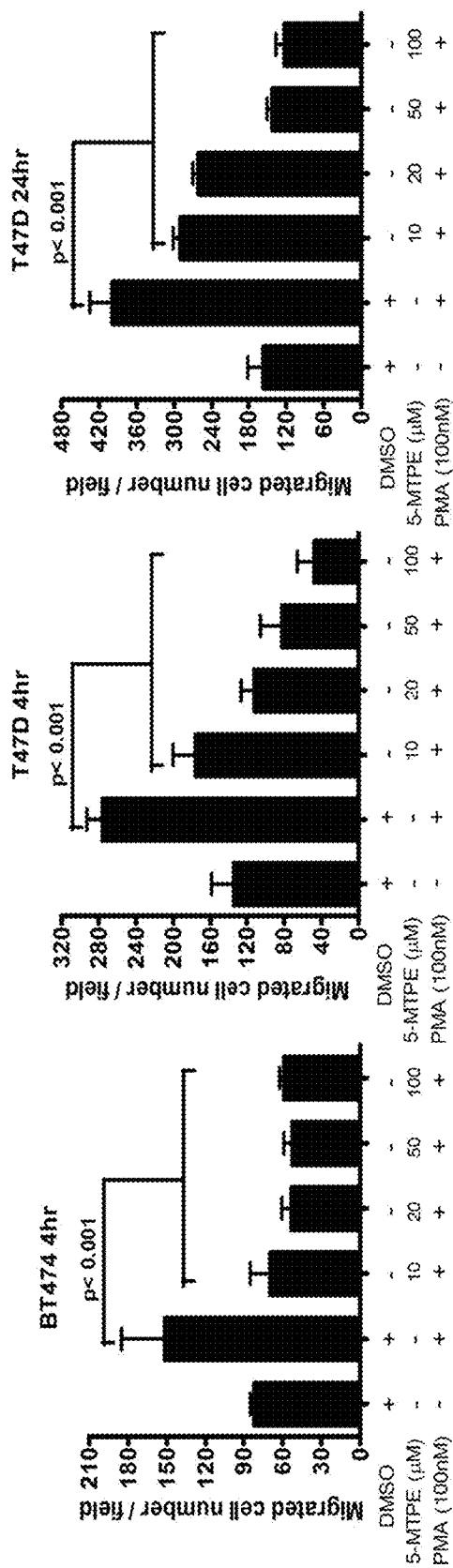
FIG. 2B shows results of cell migration assays in BT474 and T47D breast cancer cells by treating 5-MTPE.
Figure 2C:
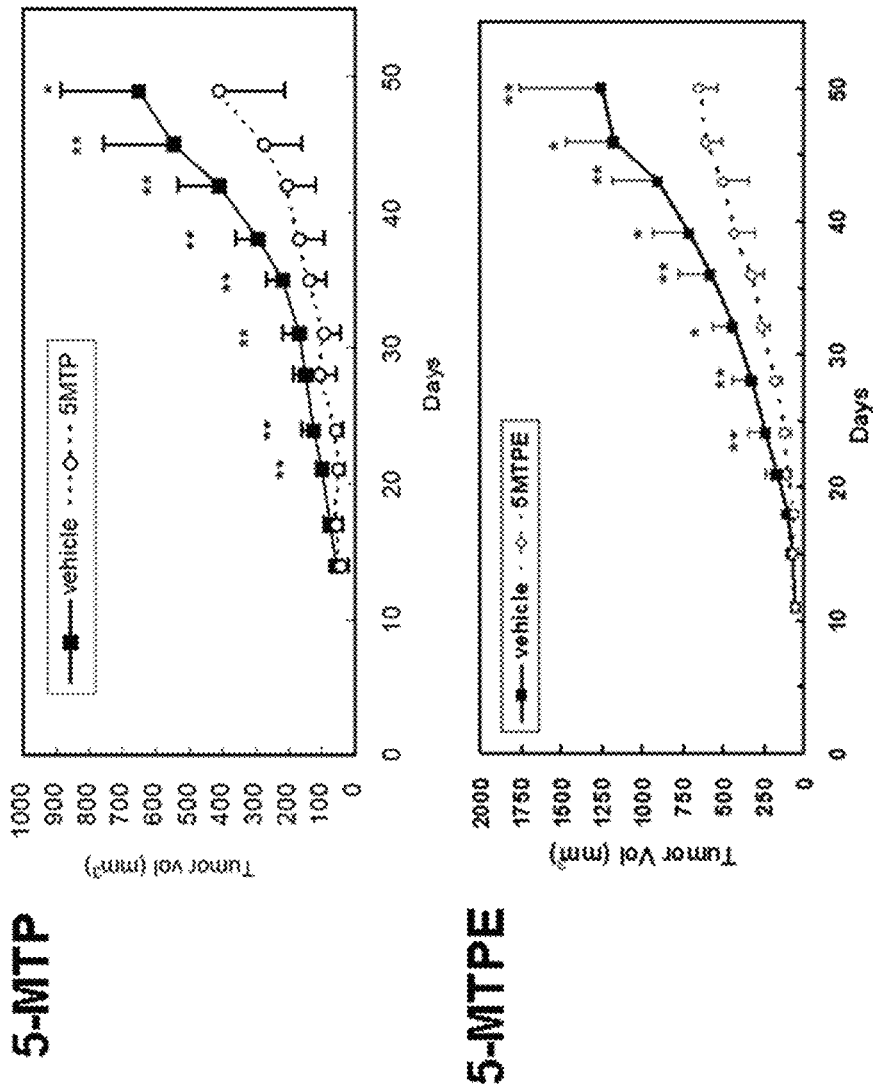
FIG. 2C shows results of tumor xenograft experiment by treating 5-MTP or 5-MTPE, wherein * denotes p<0.05, and ** donates p<0.01.

The results shown in FIGS. 2A-2C indicate the 5-MTP and its derivatives inhibit cancer migration and tumor growth in vitro and in vivo.

5-Methoxytryptophan Derivatives Inhibit LPS-Induced COX-2 Expression and Cytokine Production in Macrophages.

After pretreating mouse macrophage RAW264.7 cells with different concentrations of 5-MTP for 30 min, cells were stimulated with LPS for 8 h. Cell lysates were immunoblotted with antibodies for COX-2 or β-actin. In addition, RAW264.7 cells were transfected with COX-2 promoter-luciferase plasmid. After 24 h transfection, the cells were incubated with LPS for 8 h. Luciferase activity was measured. The experiments were repeated 3 times with similar results. The results shown in FIGS. 3A-3B confirmed that 5-MTP blocked LPS-induced COX-2 protein expression and promoter activity in a concentration-dependent manner in RAW264.7 cells.

Furthermore, peritoneal macrophages were stimulated with LPS with or without 5-MTP. After 8 h, COX-2 protein expression was determined by western blot. The experiments were repeated 3 times with similar results. The results shown in FIG. 3C indicates that 5-MTP inhibited LPS-induced COX-2 expression in primary mouse peritoneal macrophages.

Figure 3A:
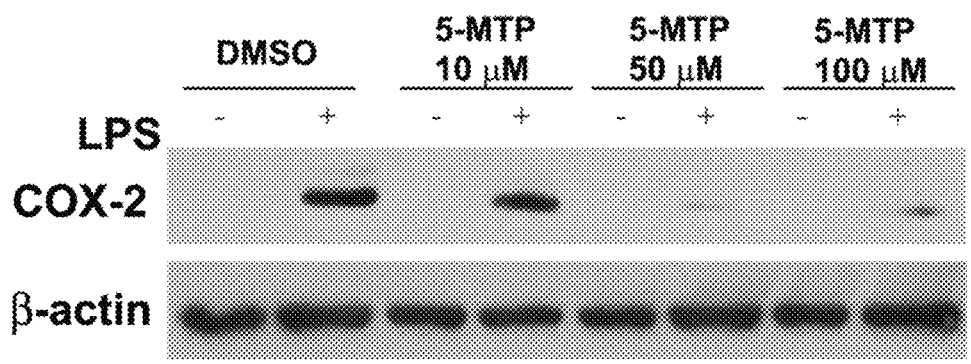
FIGS. 3A-3F respectively show inhibitions of 5-MTP on LPS-induced expression of COX-2 and different cytokines.
Figure 3B:
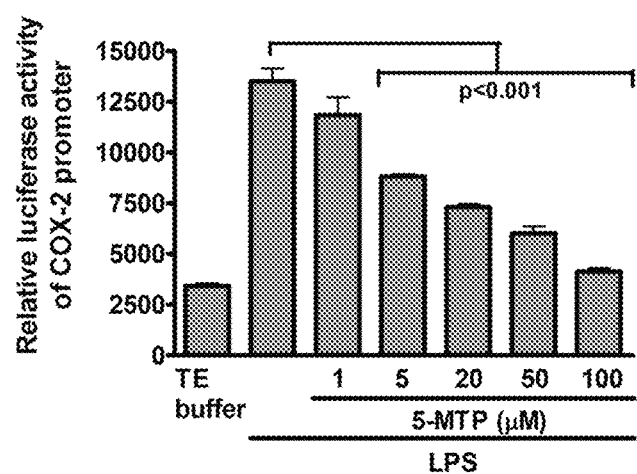
Figure 3C:
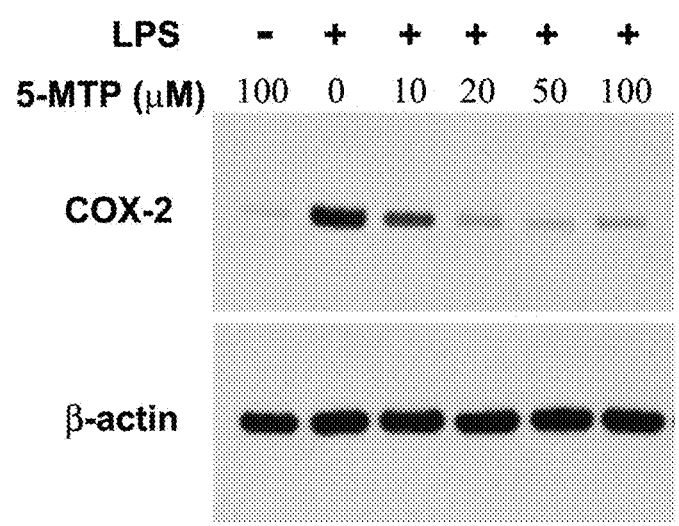
Figure 3D:
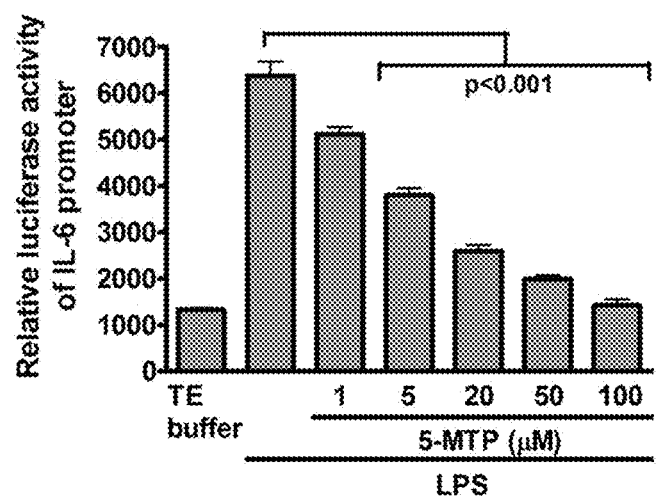
Figure 3E:
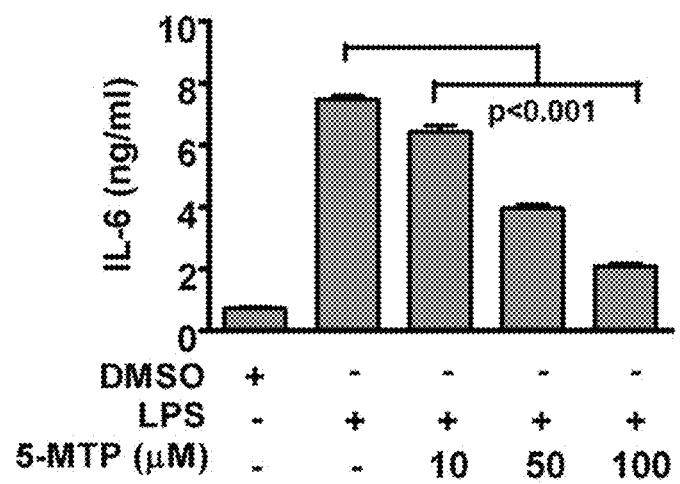

Moreover, RAW264.7 cells and IL-6 promoter-luciferase plasmid transfected RAW264.7 cells were pretreated with different concentrations of 5-MTP for 30 min, followed by LPS stimulation for 8 h. IL-6 promoter activity was measured by luciferase assay. IL-6 level in culture supernatants was measured by ELISA. According to the results shown in FIGS. 3D-3E, 5-MTP inhibited LPS-induced IL-6 promoter activity and protein expression in RAW264.7 cells in a concentration-dependent manner, comparable to its inhibition of COX-2 expression (FIGS. 3A-3B).

Figure 3F:
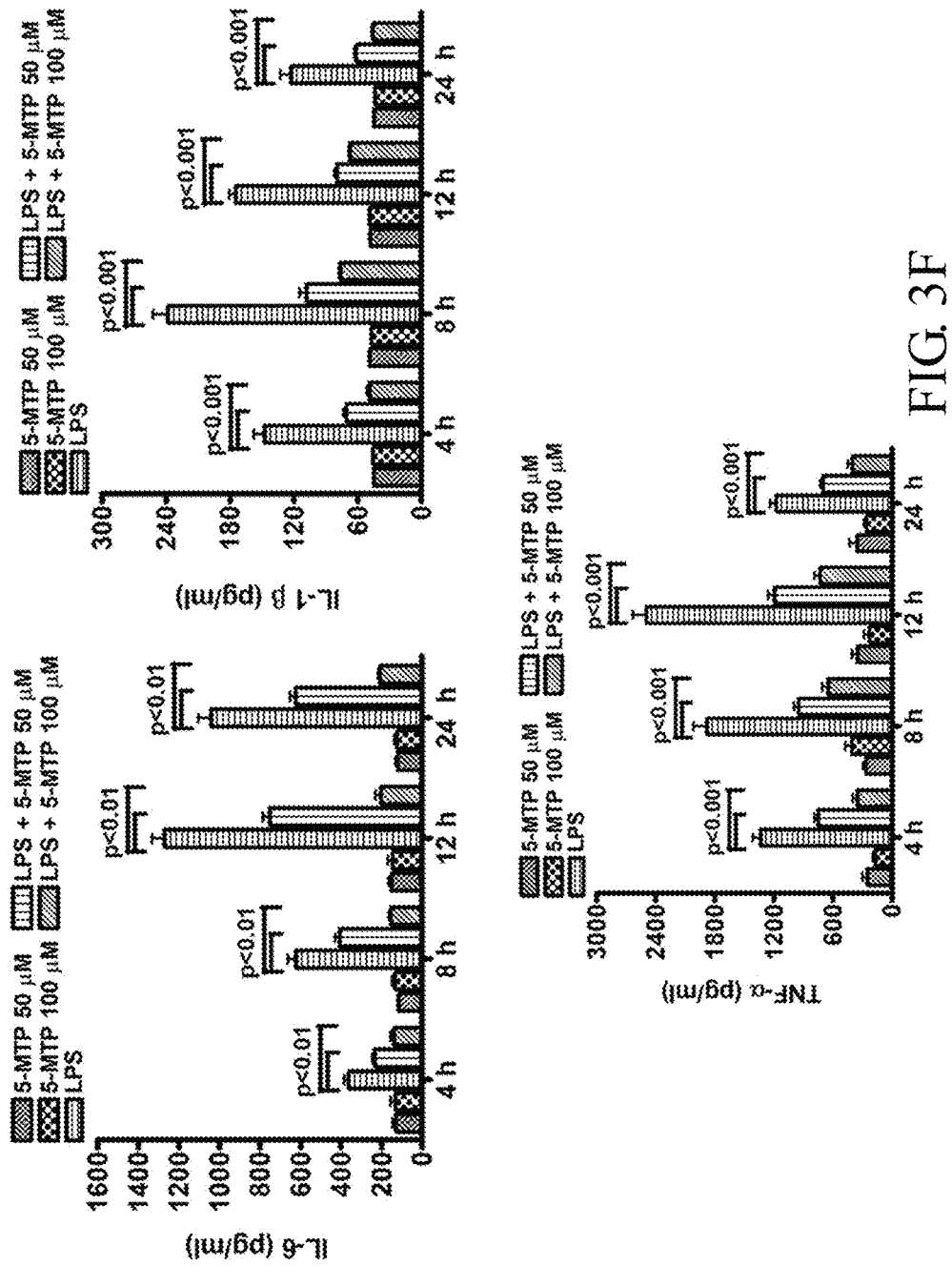

Furthermore, peritoneal macrophages were stimulated with LPS with or without 5-MTP. After 24 h, proinflammatory cytokines were measured by ELISA. The results shown in FIG. 3F indicates that 5-MTP inhibited IL-6, IL-1β and TNF-α production in peritoneal macrophages and TNF-α production in RAW264.7 cells (data not shown).

On the contrary, neither serotonin nor 5-methoxytryptamine or tryptophan exerted an effect on COX-2 and IL-6 expression levels, as shown in the following Table 2.

TABLE 2

Suppressive activity in LPS-induced cytokine production

| | |
|---|---|
| Tryptophan | – |
| Serotonin | – |
| 5-methoxytryptamine | – |
| 5-MTP | + |
| 5-MTPE | + |

Figure 4A:
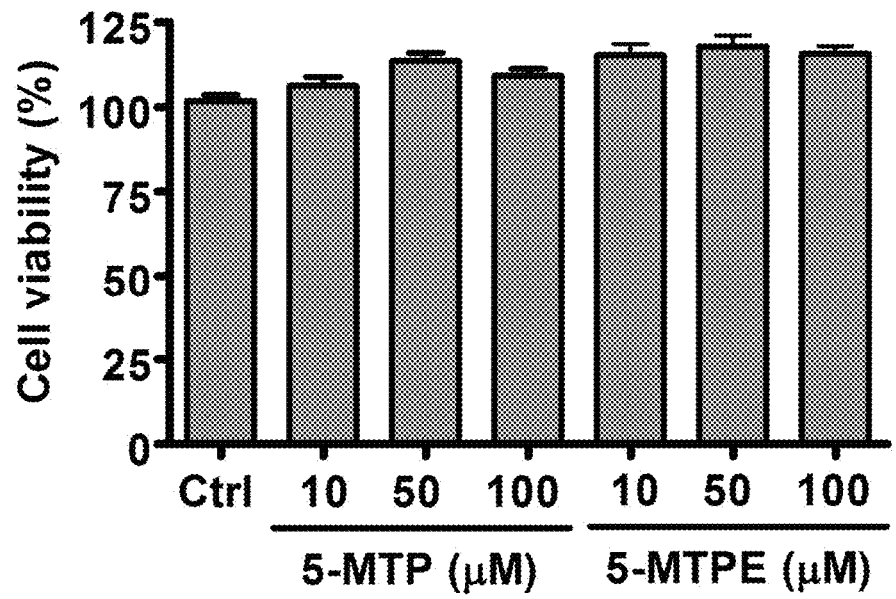
FIGS. 4A-4B shows effect of 5-MTPE on cell viability and IL-6 production.
Figure 4B:
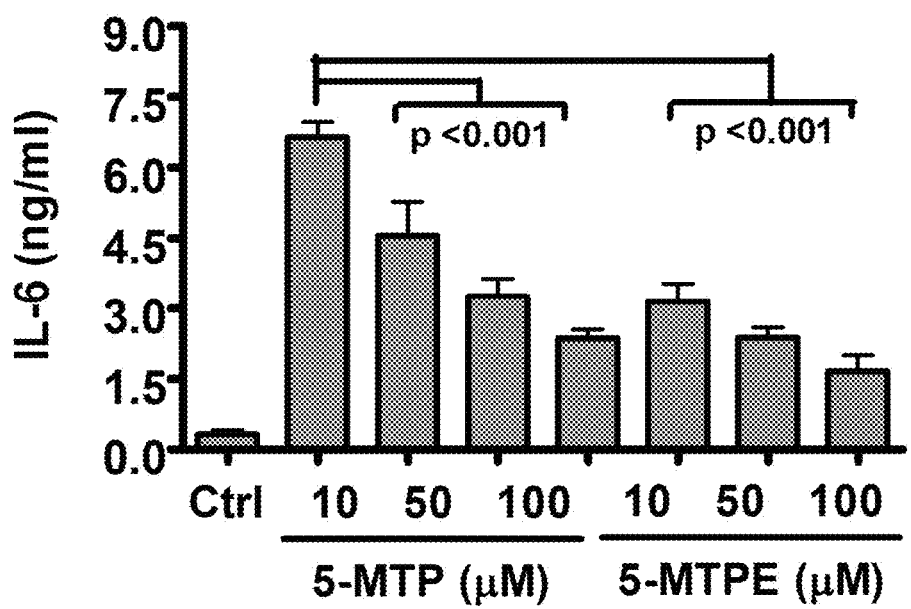

Furthermore, RAW264.7 cells were treated with different concentrations of 5-MTP or 5-MTPE for 24 h. Cell viability was determined by MTT assay. In another experiment, after pretreating RAW264.7 cells with different concentrations of 5-MTP or 5-MTPE for 30 min, cells were stimulated with LPS for 24 h. IL-6 level in culture supernatants was measured by ELISA. As shown in FIGS. 4A-4B, the 5-MTP derivatives, 5-MTPE significantly inhibited LPS-induced cytokine production but not cell viability.

From the results shown in FIGS. 3A-4B and Table 2, these results imply that the 5-methoxy-indole-3-propionic acid moiety is required for inhibiting LPS-induced COX-2 and IL-6 production. Overall, these results indicate that 5-MTP and its derivatives 5-MTPE suppresses LPS-induced inflammatory responses in mouse RAW264.7 cells and peritoneal macrophages.

5-Methoxytryptophan Derivatives Protect Against Lethal Endotoxemia in Mice.

Since suppression of 5-MTP by endotoxemia could contribute to uncontrolled macrophage overproduction of proinflammatory cytokines and mediators, we determined whether exogenous 5-MTP administration rescues mice from LPS-induced systemic inflammation, organ damage and mortality. Mice were injected with saline, 5-MTP (23.4 mg/kg), 5-MTPE (25 mg/kg) or vehicle for 30 min, followed by LPS (60 mg/kg) (saline, n=25; 5-MTP, n=7; 5-MTPE, n=7; LPS, n=30; LPS+5-MTP, n=25; LPS+5-MTPE, n=25). Survival was monitored during the next 72 h. *P<0.001 compared to LPS treatment.

Figure 5A:
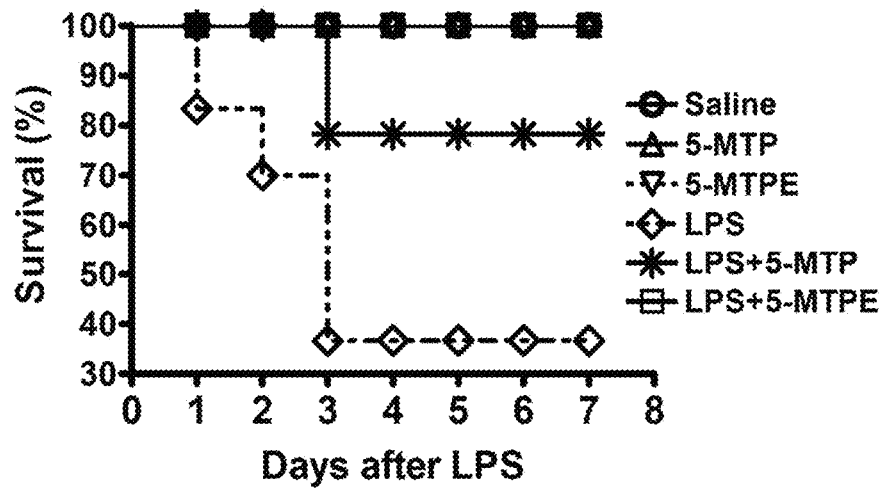
FIG. 5A shows survival of mice injected with and without 5-MTP or 5-MTPE before these animals were challenged with LPS.
Figure 5B:
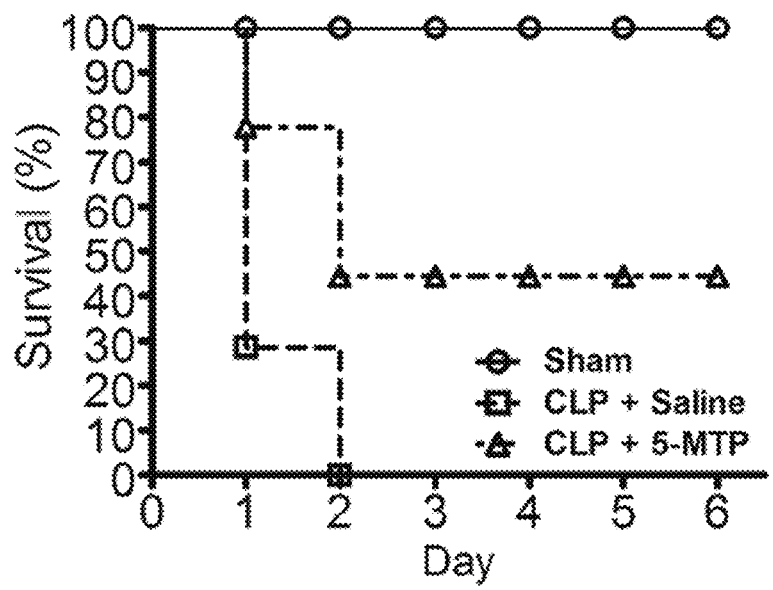
FIG. 5B shows survival of mice injected with and without 5-MTP 30 mins after cecal ligation and puncture (CLP) surgery.

As shown in FIG. 5A, mice treated with LPS started to die at day 1, and more than 65% of mice died at 72 h. By contrast, none of the mice treated with 5-MTP died at day 1 and only 20% of endotoxemic mice died at day 3 while no mortality was observed in control groups (saline or 5-MTP alone). Notably, 5-MTPE showed a 100% protective capacity in LPS-induced lethal endotoxemia. To confirm the protective effect of 5-MTP in endotoxemia, we used cecal ligation and puncture (CLP) model in mice. 5-MTP-afforded protection was also observed in mice challenged with CLP. It significantly improved survival from 0% to 44.4% at day 2. This improved survival was maintained up to day 6 (FIG. 5B).

In addition, paraffin-embedded sections were prepared from lungs of mice injected with 60 mg/kg LPS with or without saline or 5-MTP for the indicated time. Lung tissues were stained with hematoxylin and eosin and examined under light microscopy. The results are shown in FIG. 5C, in which scale bars represent 100 μm.

Figure 5C:
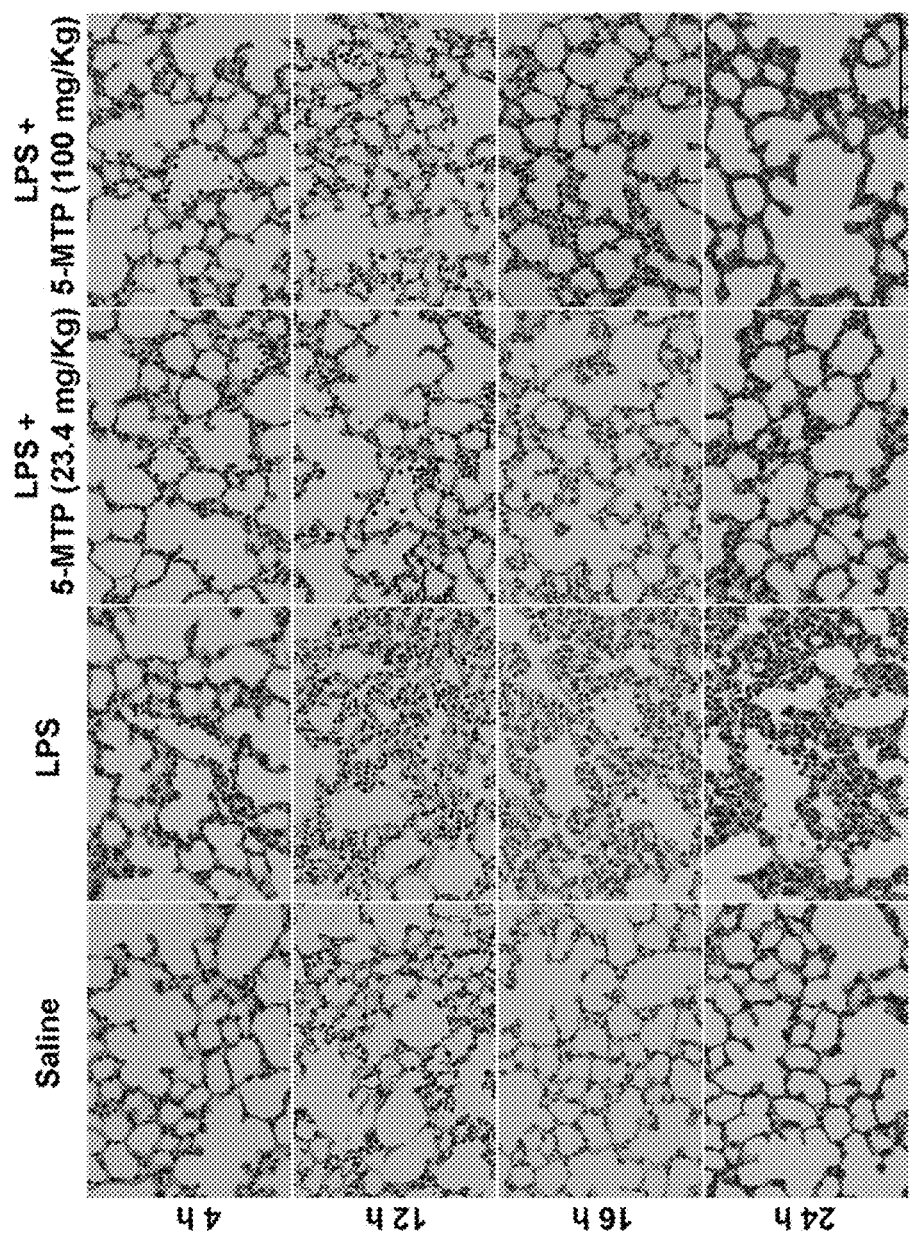
FIG. 5C shows inhibitions of 5-MTP on mice challenged with LPS.

As shown in FIG. 5C, examination of lung tissues revealed that LPS induced time-dependent progression of polymorphonuclear leukocyte infiltration, alveolar septal wall thickening, interstitial edema, and alveolar congestion, consistent with pathological changes of sepsis. 5-MTP significantly alleviated these pathological changes caused by LPS.

Furthermore, bronchoalveolar lavage fluid (BALF) was isolated from mice treated with LPS with or without various concentrations of 5-MTP for 24 h. Cell number in BALF was determined by trypan blue exclusion assay.

Figure 5D:
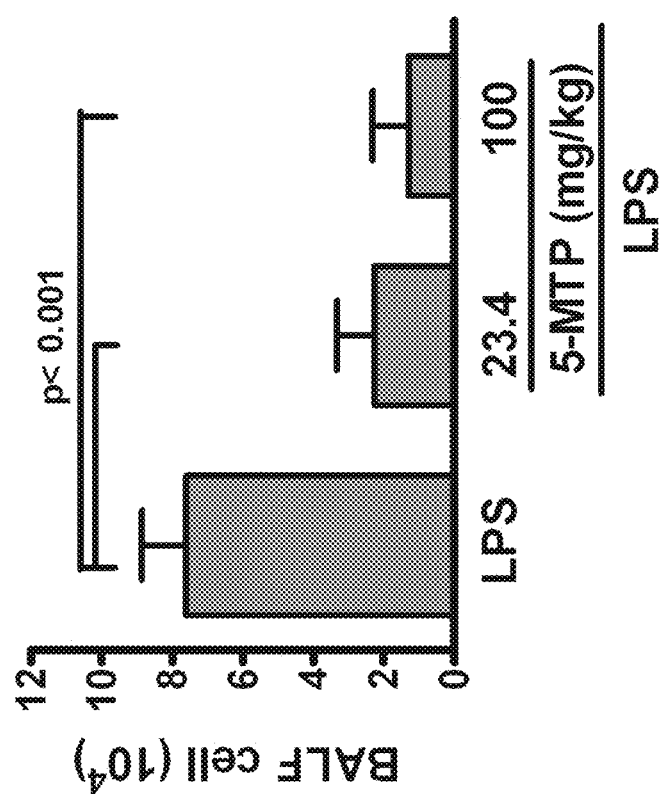
FIG. 5D shows results of bronchoalveolar lavage fluid (BALF).

As shown in FIG. 5D, at 24 h after LPS administration, there was a significant increase in total cell number in the bronchoalveolar lavage fluid (BALF), which was reduced by 5-MTP in a dose-dependent manner.

Figure 6A:
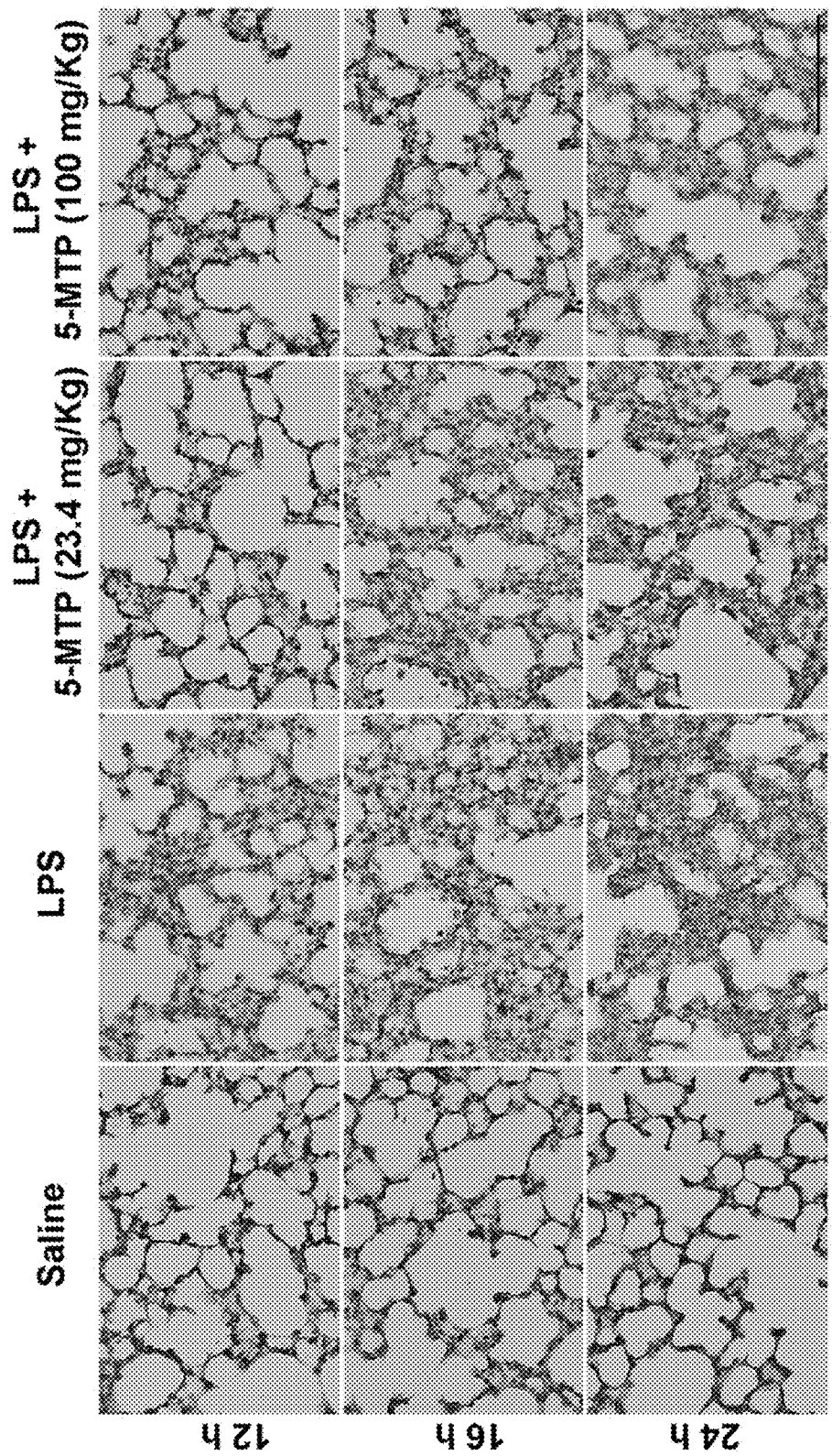
FIGS. 6A-6B show inhibitions of 5-MTP on LPS-induced expression of COX-2 and iNOS.
Figure 6B:
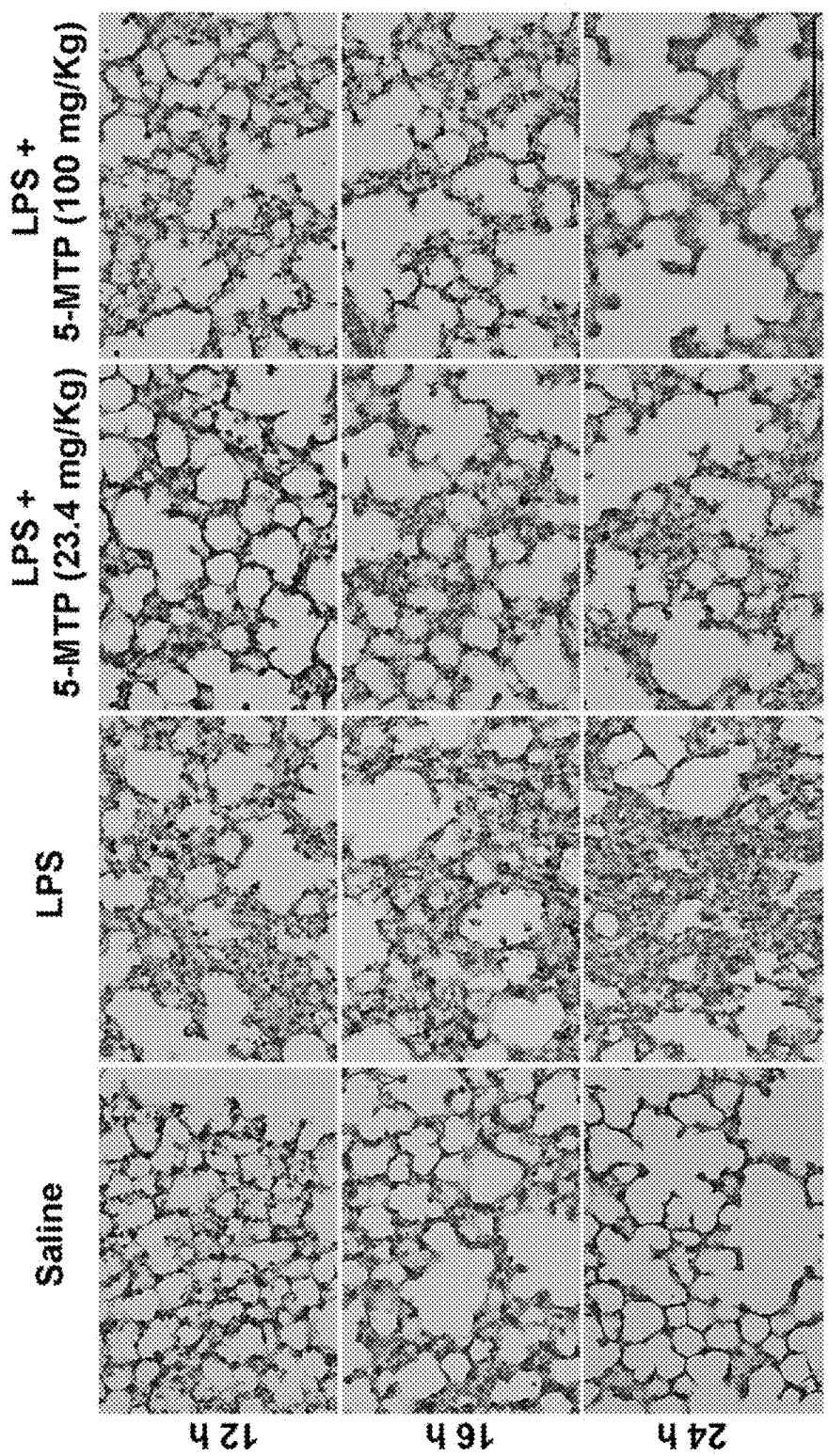

Moreover, paraffin-embedded sections were prepared from lungs of mice injected with 60 mg/kg LPS with or without saline or 5-MTP at 12 h, 16 h and 24 h. COX-2 and inducible nitric oxide synthase (iNOS) protein levels in lung tissues were determined by immunohistochemistry by staining with anti-COX-2 and anti-iNOS antibodies, respectively. The results are shown in FIGS. 6A-6B, in which scale bars represent 100 μm. As shown in FIGS. 6A-6B, 5-MTP suppresses COX-2 (FIG. 6A) and iNOS (FIG. 6B) expression in lung tissues of LPS-induced endotoxemia, which is consistent with the results that 5-MTP suppresses macrophage COX-2 expression and cytokine productions (especially; iNOS productions).

Mice were injected intraperitoneally with or without different concentrations of 5-MTP or saline for 30 min, followed by LPS administration for the indicated time. Proinflammatory cytokines level in serum was measured by ELISA. (n=6 per group). The result shown in FIGS. 7A-7D respectively indicates that 5-MTP abated the elevation of blood level of IL-1β, TNF-α, IL-6 and INF-κ in LPS-treated mice in a dose- and time-dependent manner. Also, 5-MTP at 23.4 mg/kg significantly reduced all the tested cytokines and at 100 mg/kg it reduced the cytokines to the basal level. In addition, 5-MTP suppressed the rise of IL-12 in LPS-treated mice (data not shown). These results suggest that 5-MTP protects against LPS-induced lung damages and mortality by preventing cytokine, prostaglandin and NO storm.

Figure 7A:
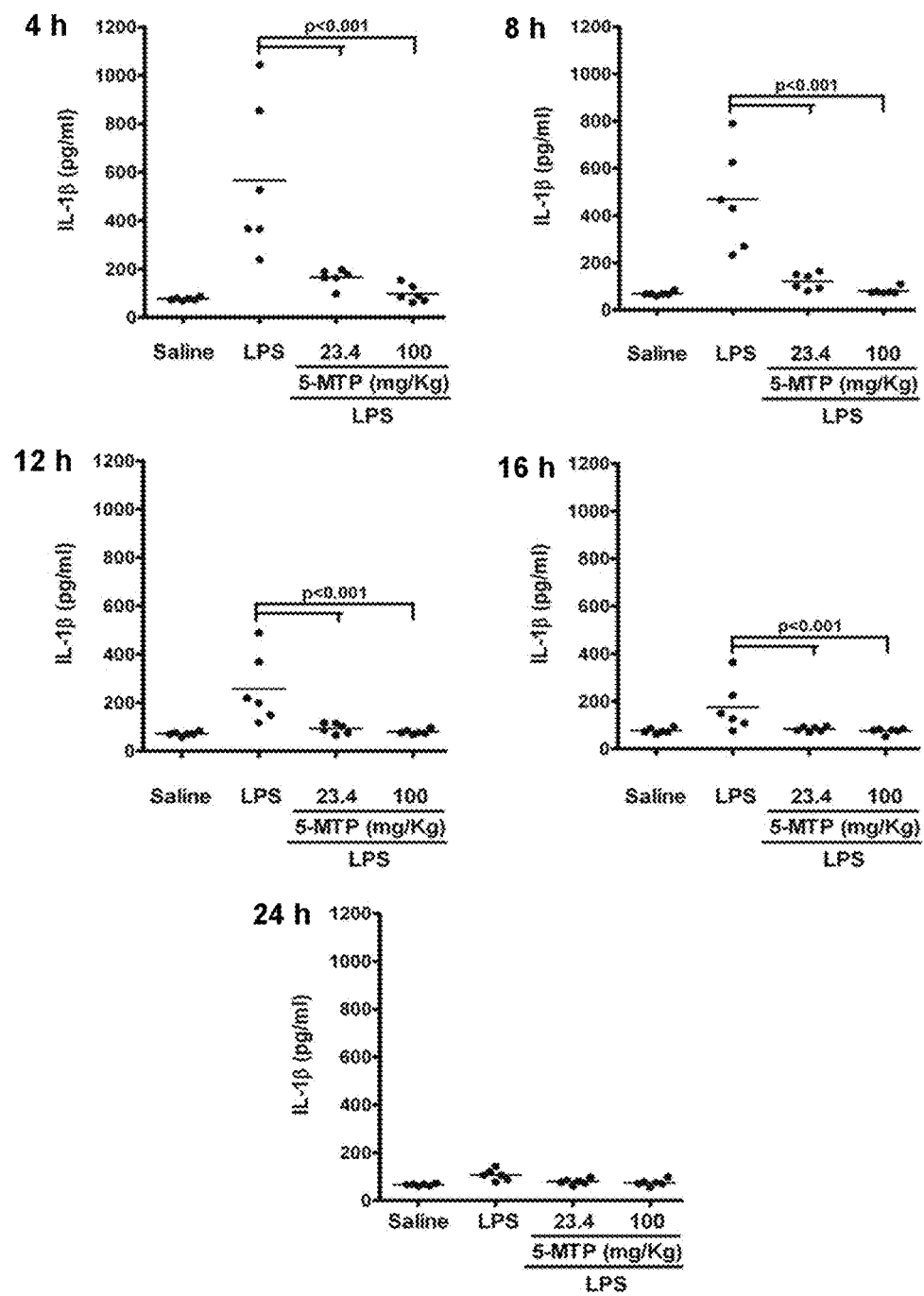
FIGS. 7A-7D respectively show different proinflammatory cytokines levels in mice treated with or without 5-MTP.
Figure 7B:
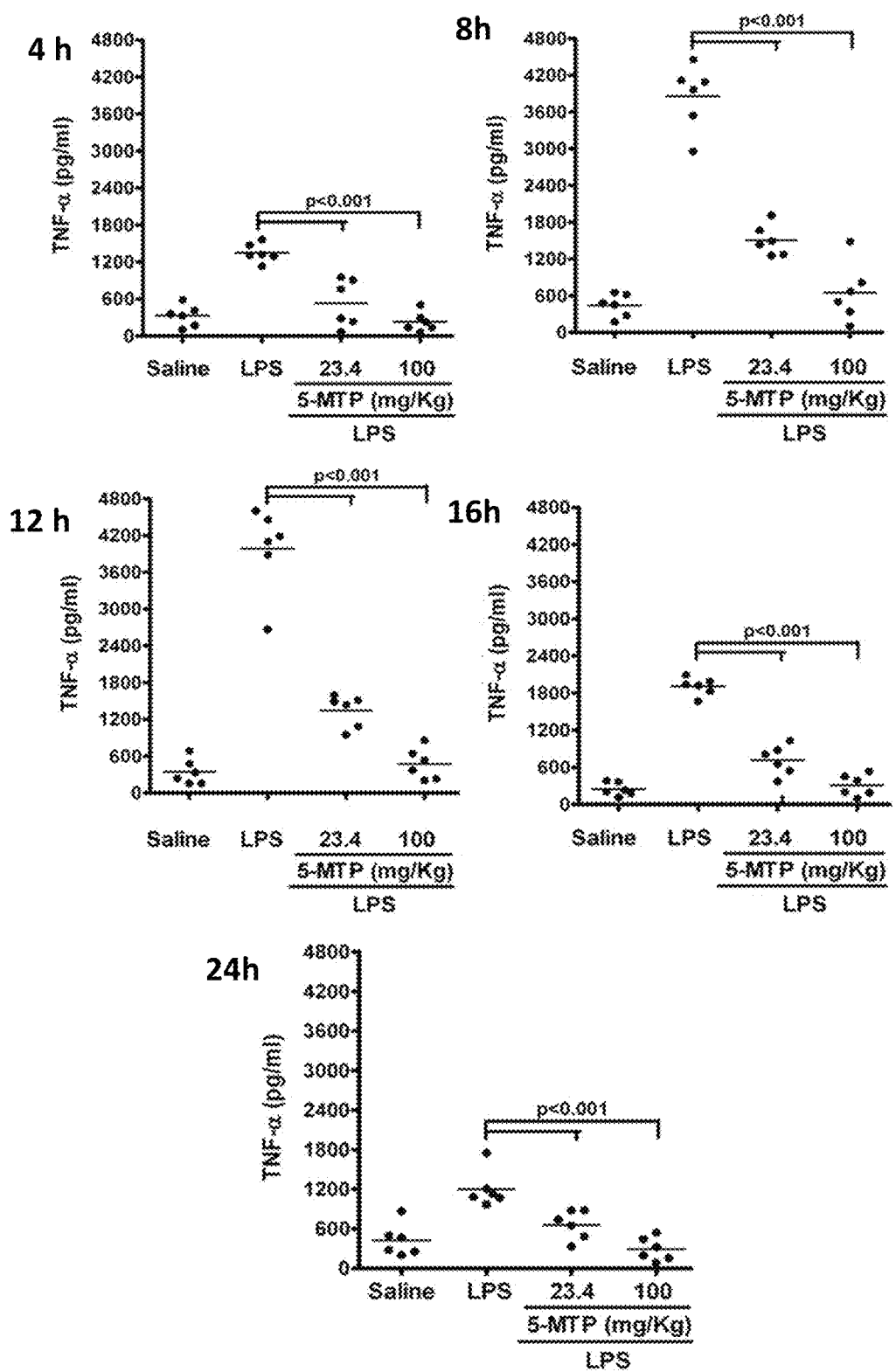
Figure 7C:
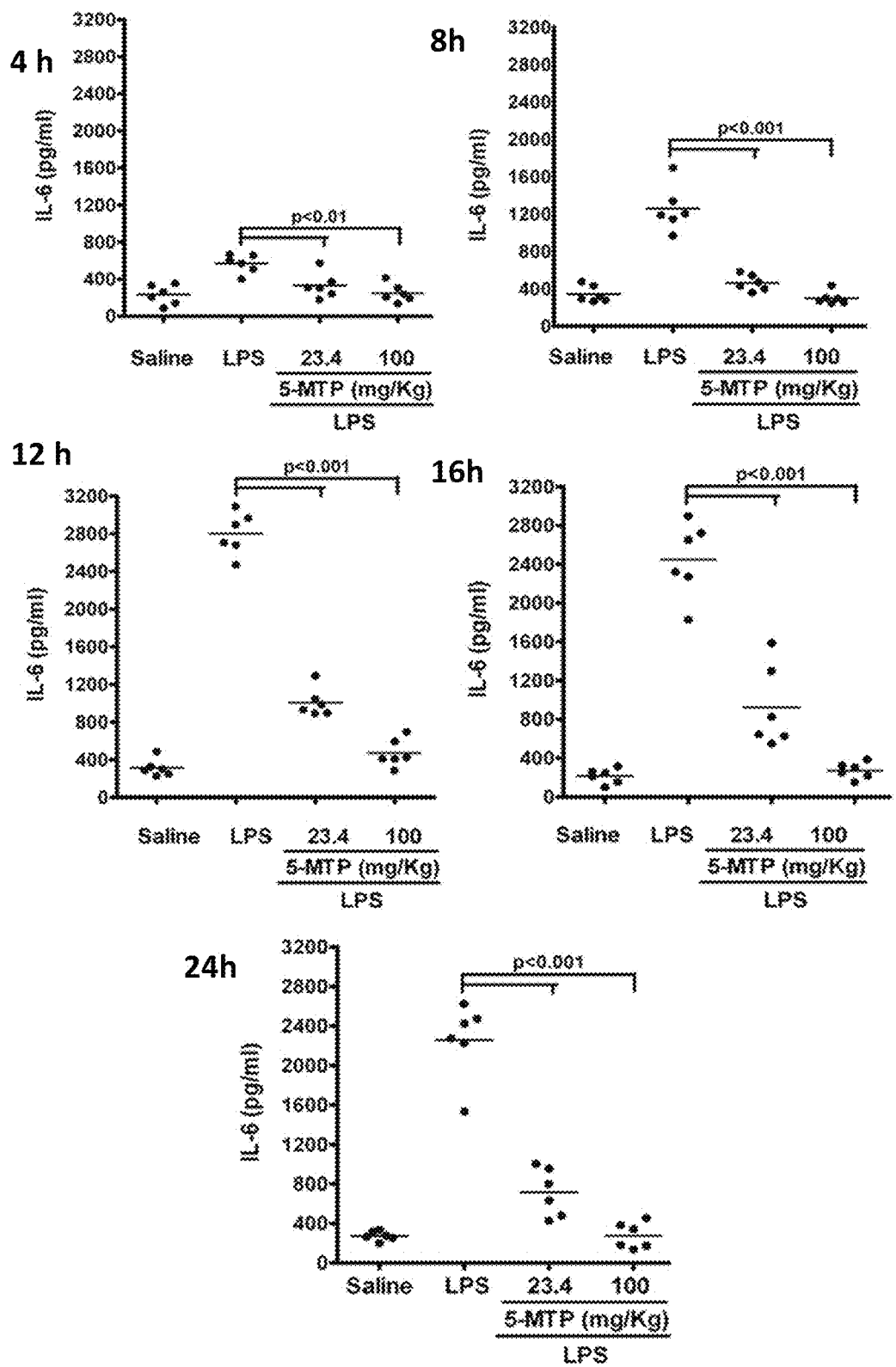
Figure 7D:
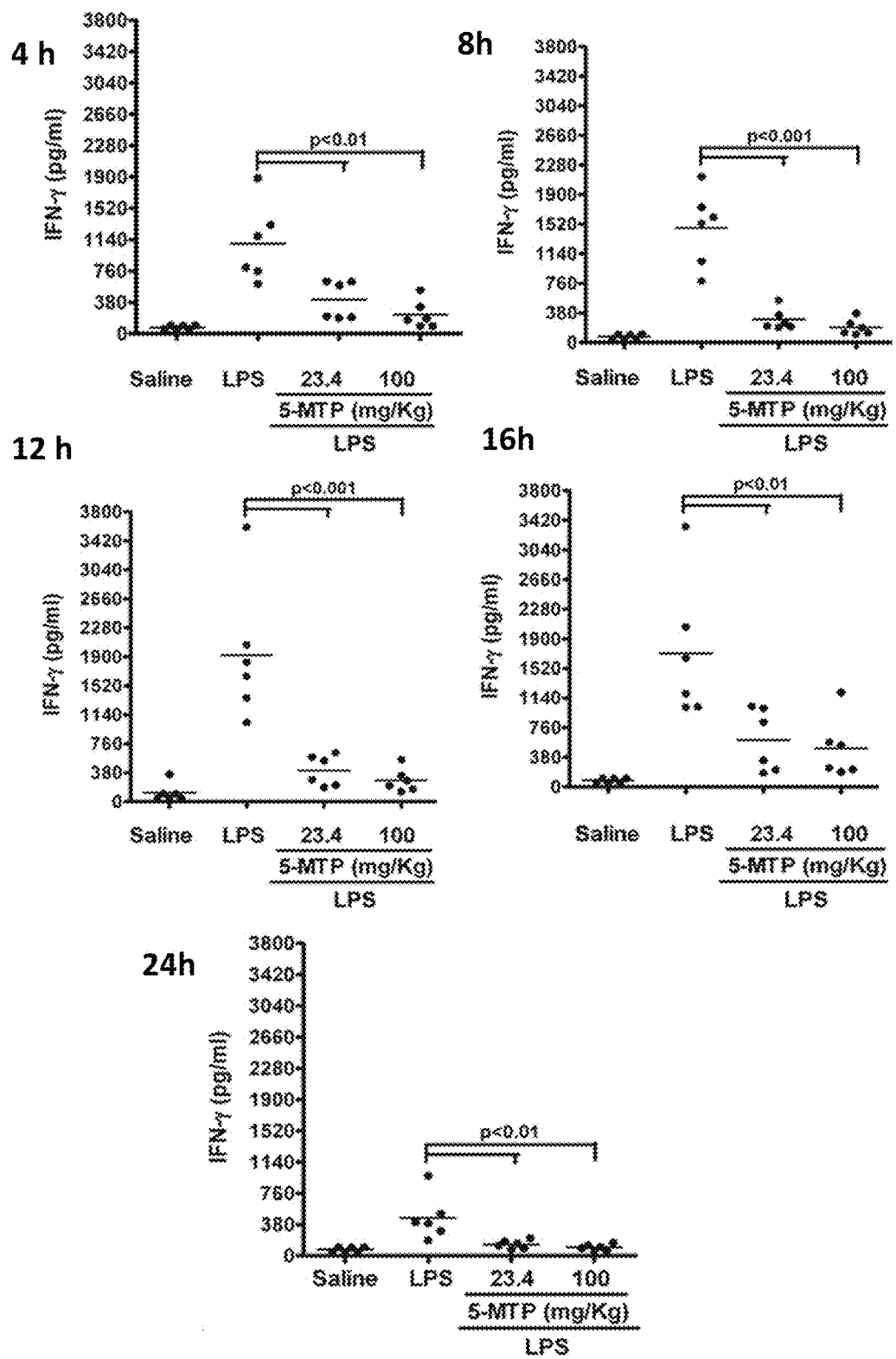
Figure 7E:
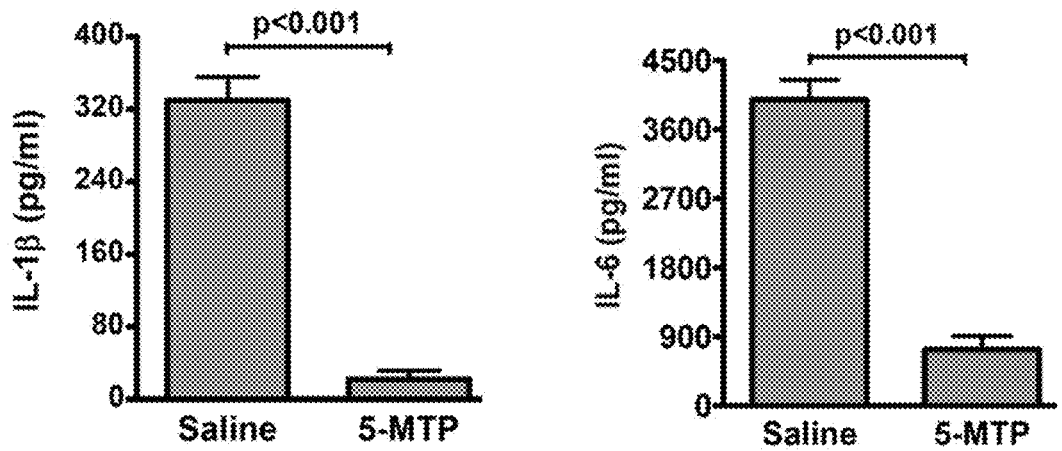
FIG. 7E shows proinflammatory cytokines levels in peritoneal macrophages treated with or without 5-MTP.

To further confirm that 5-MTP deactivates peritoneal macrophages during endotoxemia, we evaluated the effect of 5-MTP on IL-1β and IL-6 production ex vivo in peritoneal macrophages isolated from untreated or 5-MTP-treated endotoxemic mice. Peritoneal macrophages were isolated 8 h after LPS injection with saline or 5-MTP (23.4 mg/kg) and cultured with medium alone. After 24 h, proinflammatory cytokines were measured by ELISA (n=3). As show in FIG. 7E, macrophages from untreated mice spontaneously produced high amounts of IL-1β and IL-6, both of which were significantly suppressed by 5-MTP.

Figure 7F:
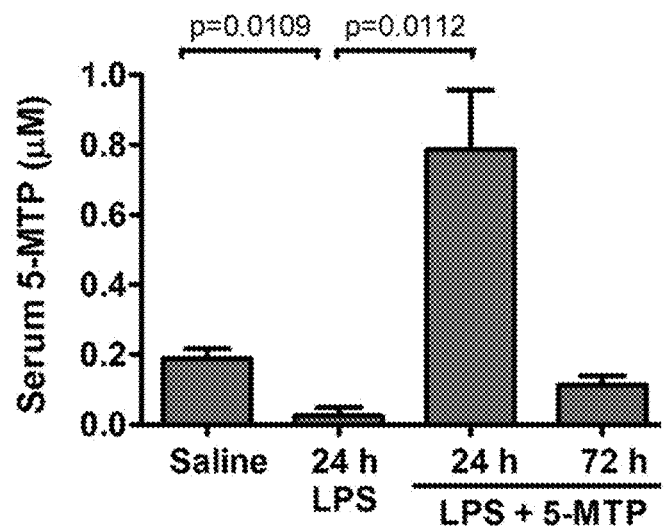
FIG. 7F shows serum 5-MTP levels in mice treated with saline or LPS with or without 5-MTP.

To ensure that 5-MTP administration increases serum 5-MTP, we analyzed 5-MTP level at 24 h and 72 h after 5-MTP infusion. Serum 5-MTP concentrations in mice treated with saline or LPS with or without 5-MTP (23.4 mg/kg) at 24 h and 72 h. The error bars denote mean±SD (n=3). As shown in FIG. 7F, serum 5-MTP remained highly elevated, several-fold over the basal level at 24 h after 5-MTP administration and returned to basal level at 72 h.

These results support the notion that 5-MTP suppression by LPS contributes to systemic inflammation, lung damage and death, and supplement with 5-MTP to boost the level of 5-MTP confers control of systemic inflammation and protection against tissue damage and death.

5-MTP Reduces Neutrophil Infiltration and Chemokine Production.

Figure 8A:
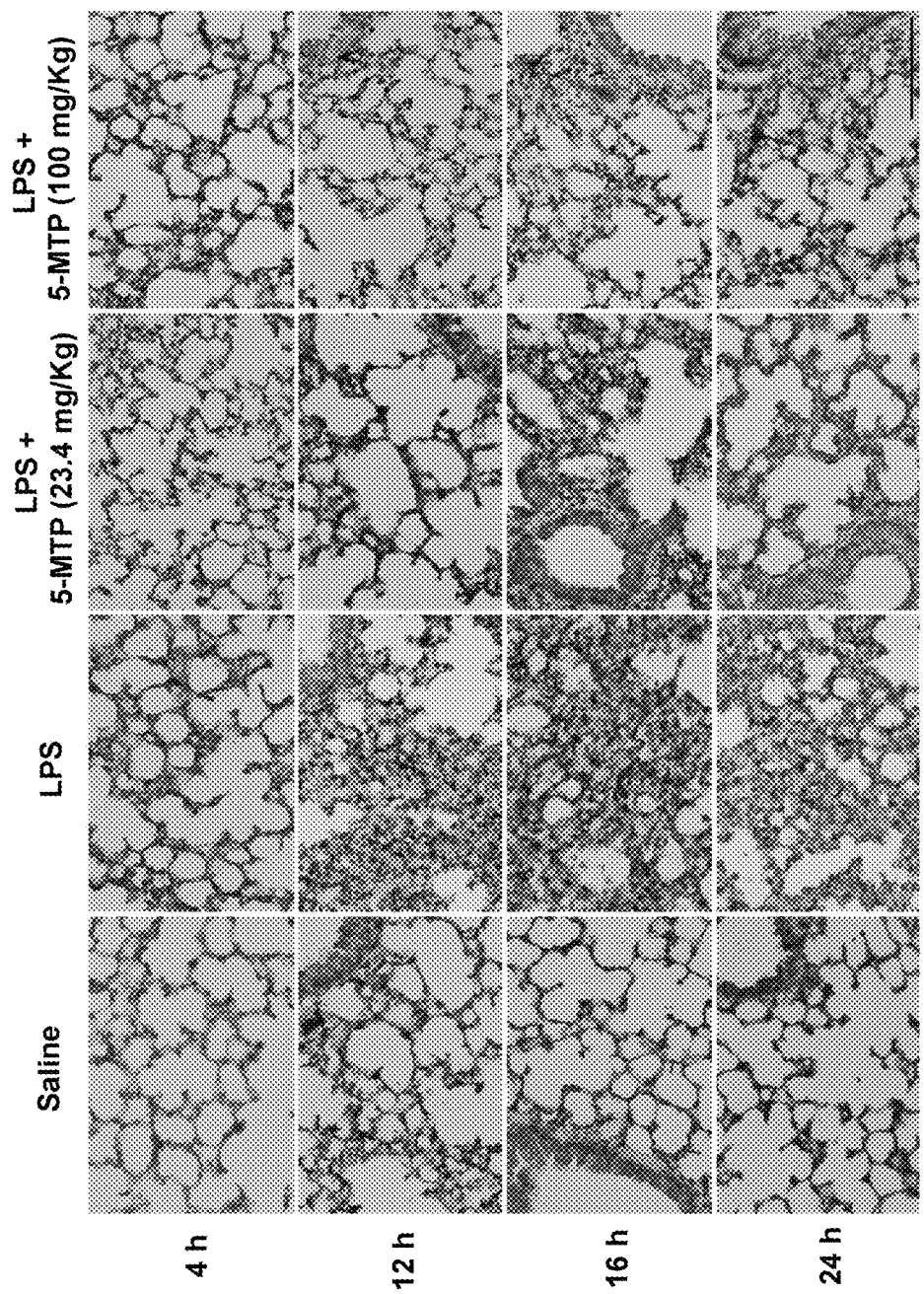
FIG. 8A shows inhibitions of 5-MTP on neutrophil infiltration.

Thirty min after saline or 5-MTP administration, mice were injected intraperitoneally with LPS at 4 h, 12 h, 16 h and 24 h. Paraffin-embedded lung tissue specimens were subjected to immunohistochemical Ly6G staining for determination of neutrophil infiltration in lung tissues. The results are shown in FIG. 8A, in which scale bars represent 100 μm. As shown in FIG. 8A, neutrophil infiltration was slightly increased at 4 h and became markedly increased at 12 h and thereafter following LPS treatment. Also, 5-MTP dose-dependently reduced neutrophil infiltration; and at 100 mg/kg, it reduced the infiltration almost to the basal level.

Figure 8B:
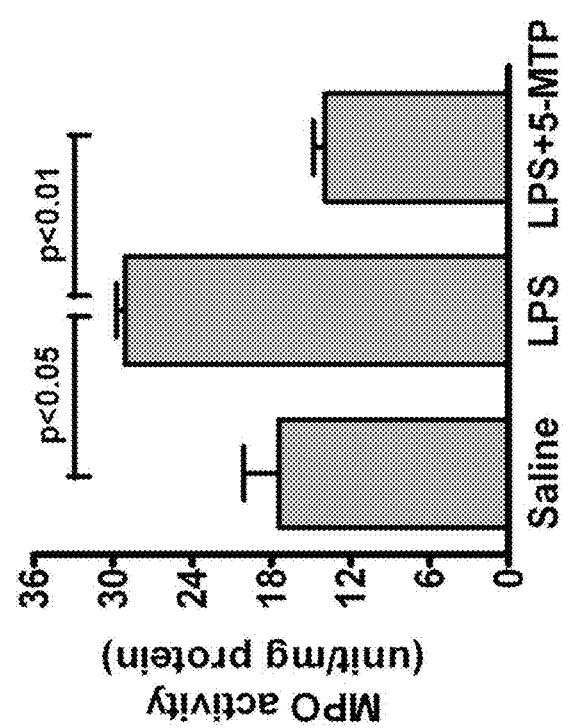
FIG. 8B shows MPO activity in lung tissues of mice treated with saline or LPS with or without 5-MTP.

In addition, MPO activity was determined in lung tissues of mice treated with saline or LPS in the presence or absence of 5-MTP (23.4 mg/kg) for 16 h (n=6 mice/group). As shown in FIG. 8B, analysis of lung MPO activity confirmed that 5-MTP reduced neutrophil infiltration to the basal level.

Furthermore, chemokine level was measured by ELISA in the serum of saline or LPS-injected mice with or without saline or 5-MTP (23.4 mg/kg) after 24 h (n=10). The results shown in FIG. 8C indicate that LPS-induced elevation of chemokines, CXCL1, MCP-1, RANTES and eotaxin in the serum was blunted by 5-MTP treatment at 24 h.

Figure 8C:
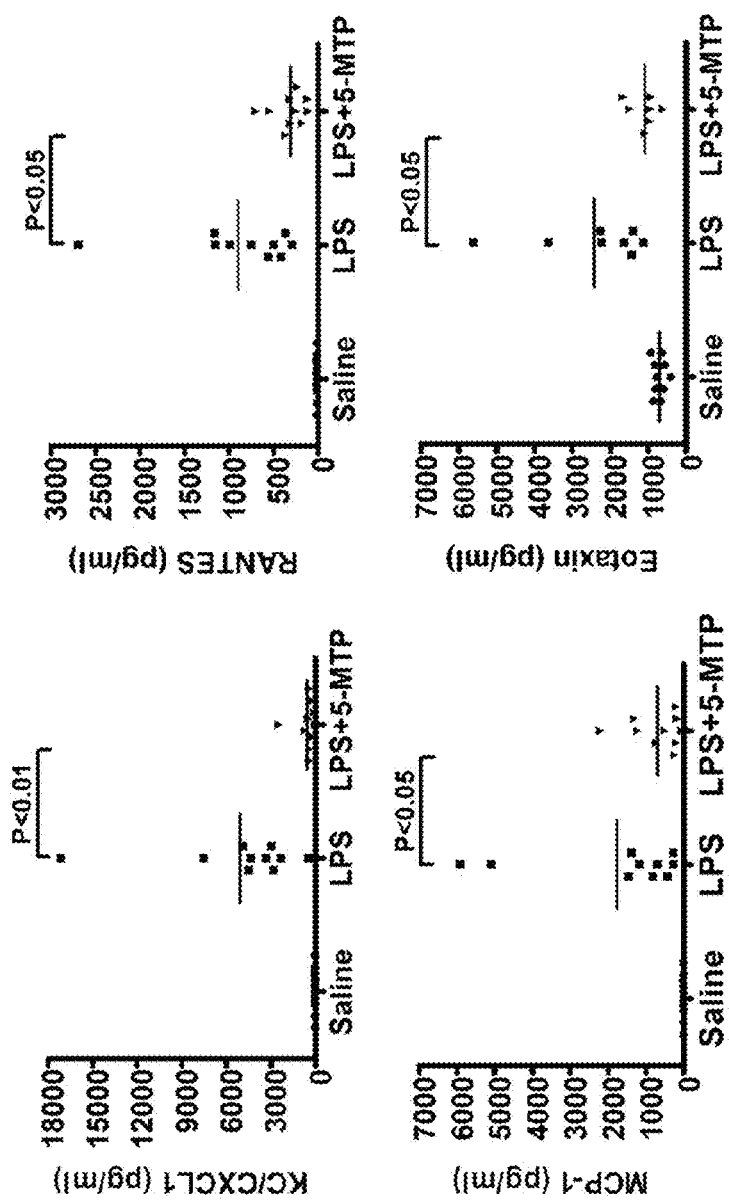
FIG. 8C shows serum chemokine levels in mice treated with saline or LPS with or without 5-MTP.

The results shown in FIGS. 8A-8C suggest that 5-MTP reduces sepsis-mediated lung damage by suppressing macrophage activation and cytokine production as well as reducing neutrophil infiltration and multiple proinflammatory chemokine production.

5-MTP Prevents LPS-Induced Lung and Spleen Cell Apoptosis.

Figure 9A:
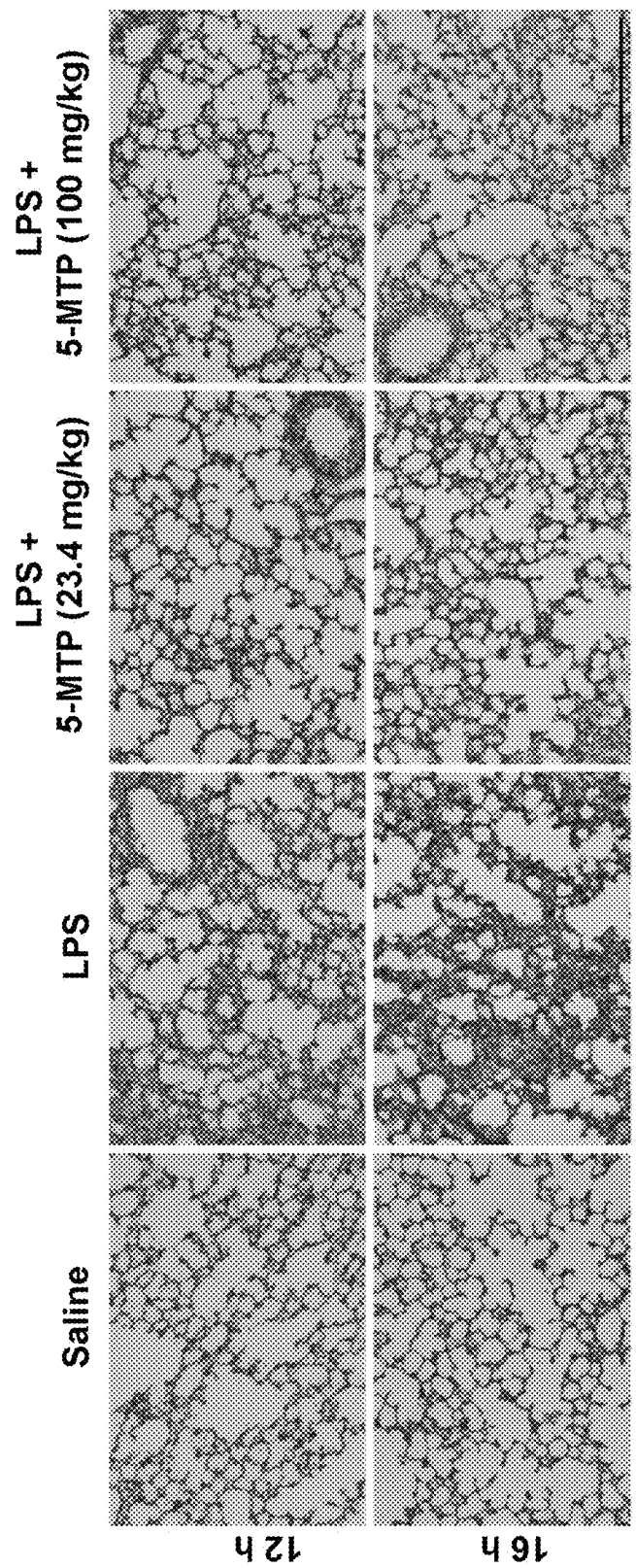
FIG. 9A shows activated caspase-3 level in lung tissues of mice treated with saline or LPS with or without 5-MTP.

Paraffin-embedded sections were prepared from lung tissues of mice treated with saline or LPS (60 mg/kg) with or without various concentrations of 5-MTP for 12 or 16 h. Activated caspase-3 level in lung tissues was determined by immunohistochemical staining of cleaved caspase-3. The results are shown in FIG. 9A, in which scale bars represent 200 μm. As shown in FIG. 9A, LPS treatment resulted in a significant increase in apoptosis as demonstrated by increased cleaved caspase-3 at 12 and 16 h which was reduced by 5-MTP.

Figures 9B, 9C:
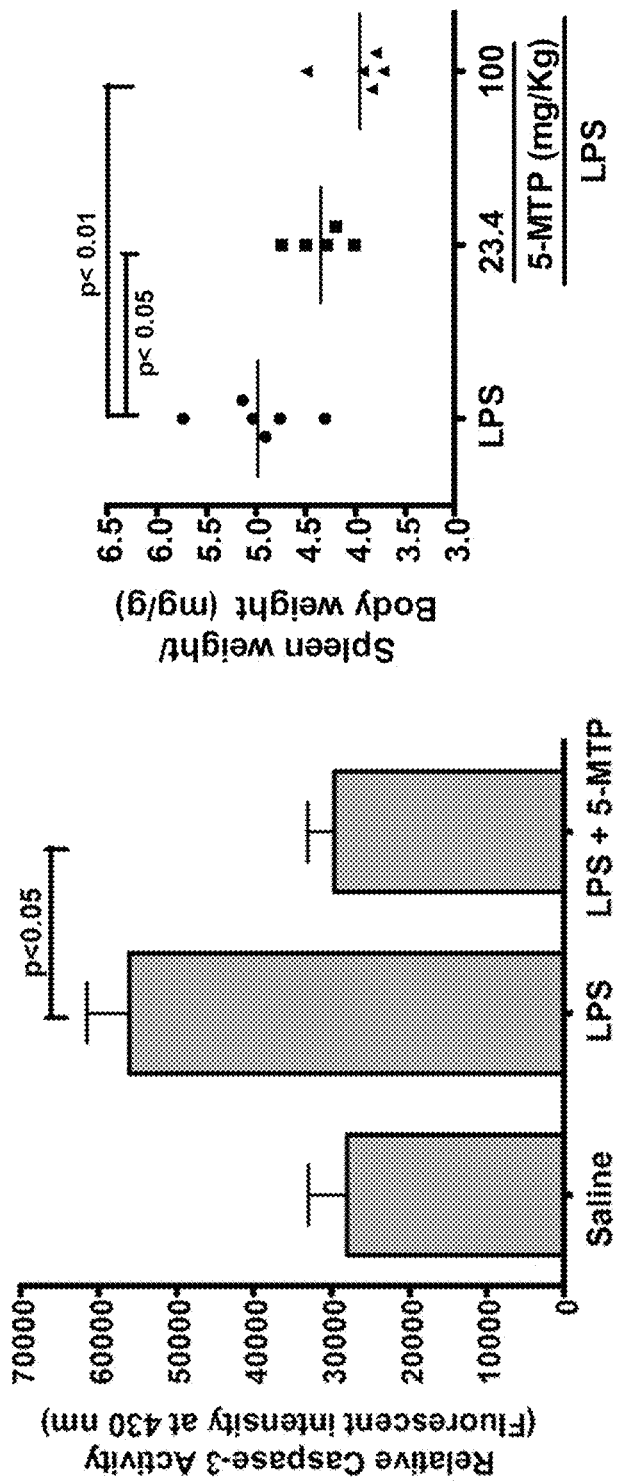
FIG. 9B shows activated caspase-3 level in splenocytes of mice treated with saline or LPS with or without 5-MTP.
FIG. 9C shows spleen weight/body weight ratio of LPS induced-mice treated with or without 5-MTP.

In addition, caspase-3 activity in splenocytes of mice treated with saline, LPS or LPS plus 5-MTP (100 mg/kg) for 16 h was measured by fluorogenic substrate as described above. The results are shown in FIG. 9B, in which the error bare denotes mean±SD (n=6 mice/group). As shown in FIG. 9B, 5-MTP also prevented LPS-induced caspase-3 cleavage in spleen cells.

Furthermore, spleen weight/body weight (SW/BW) ratio was also assessed (n=6 mice/group). As shown in FIG. 9C, in LPS-challenged mice, the spleen weight/body weight (SW/BW) ratio was markedly increased as compared with that of saline-treated mice, consistent with severe spleen edema. 5-MTP administration ameliorated spleen edema in a dose-dependent manner.

According to the results shown in FIGS. 9A-9C, these results suggest that 5-MTP prevents LPS-induced lung and spleen cell apoptosis in endotoxemic mice.

5-MTP Suppresses LPS-mediated Immune Signaling.

Figure 10A:
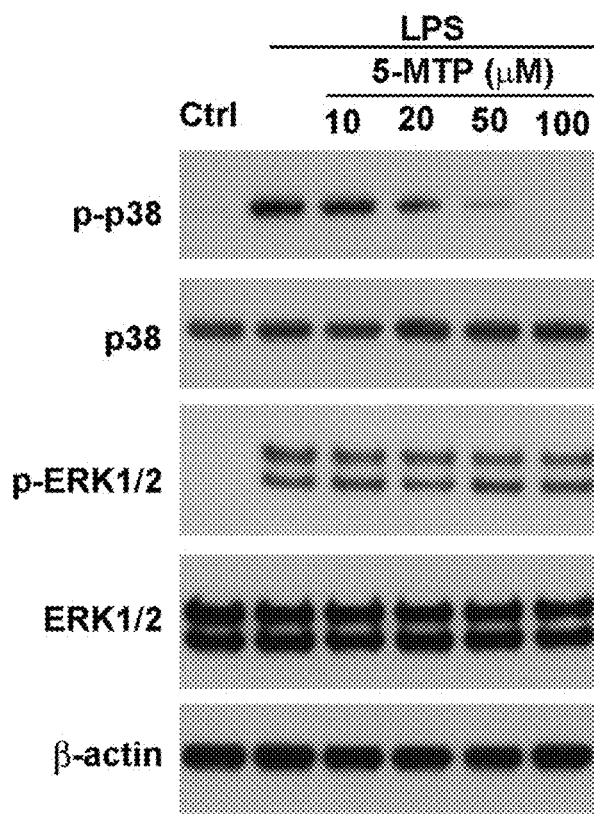
FIG. 10A shows immunoblotted results of p38, phospho-p38 (p-p38), ERK½, phospho-ERK½(p-ERK½) or β-actin in RAW264.7 cells treated with or without 5-MTP.

After pretreating RAW264.7 cells with different concentrations of 5-MTP for 30 min, cells were stimulated with LPS for 4 h. Cell lysates were immunoblotted with antibodies for p38, phospho-p38 (p-p38), ERK½, phospho-ERK½ (p-ERK½) or β-actin. As shown in FIG. 10A, 5-MTP dose-dependently blocked the phosphorylation of p38 MAPK but not that of ERK½ in LPS-treated RAW264.7 cells. Activation of p38 MAPK in macrophages is required for TLR-induced NF-κB activation, which is one of the key factors affecting TLR-induced cytokine production. Thus, we evaluated the effect of 5-MTP on LPS-induced. NF-κB activation.

Figure 10B:
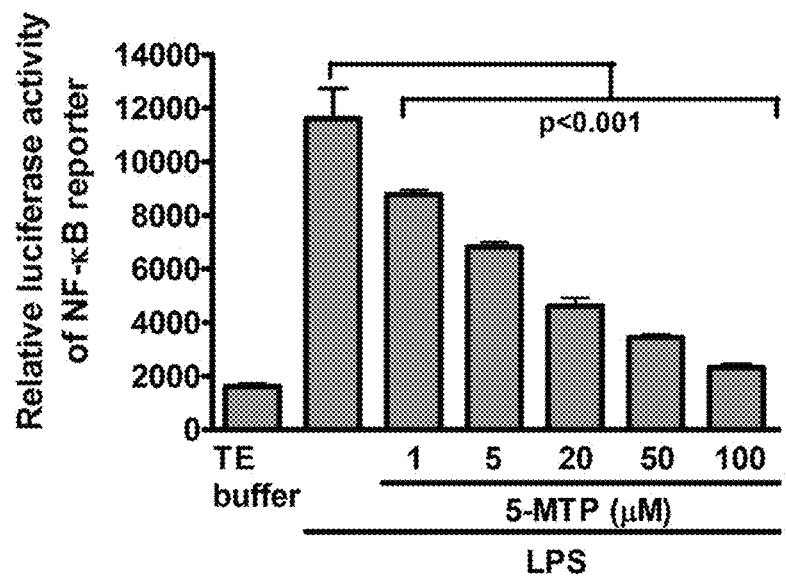
FIG. 10B shows NF-κB promoter activity W264.7 cells treated with or without 5-MTP.

After pretreating RAW264.7 cells with different concentrations of 5-MTP for 30 min, cells were stimulated with LPS for 8 h. NF-κB promoter activity as measured by NF-κB promoter-luciferase assay. As shown in FIG. 10B, 5-MTP suppressed NF-κB transactivation in a concentration-dependent manner.

Figure 10C:
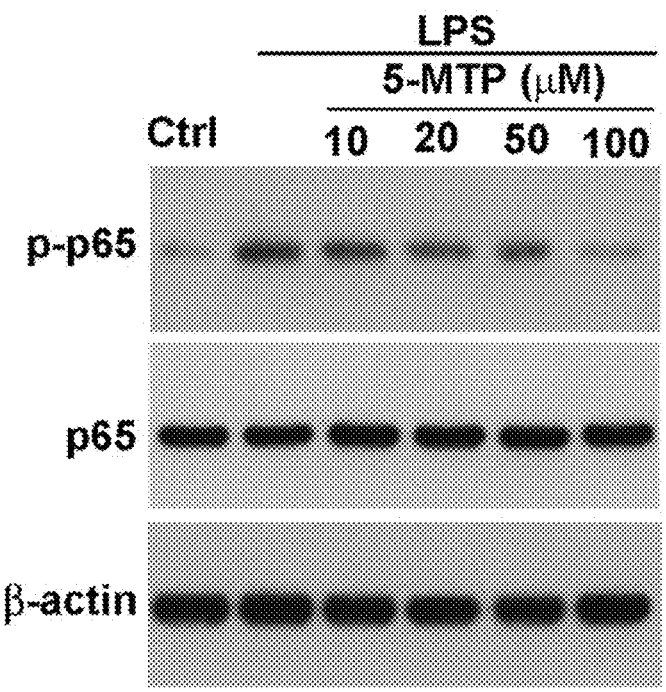
FIG. 10C shows immunoblotted results of NF-κB p65, phospho-NF-κB p65 (p-p65) (Ser536) or β-actin in RAW264.7 cells treated with or without 5-MTP.
Figure 10D:
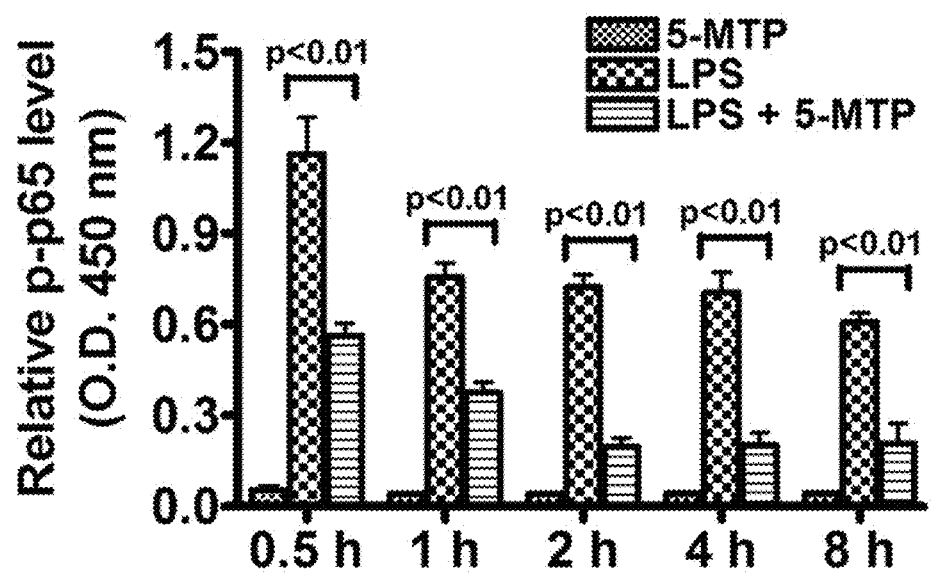
FIG. 10D shows phosphor-p65 level in the lysates of peritoneal macrophages treated with LPS with or without 5-MTP.

Furthermore, after pretreating RAW264.7 cells with different concentrations of 5-MTP for 30 min, cells were stimulated with. LPS for 4 h. NF-κB p65, phospho-NF-κB p65 (p-p65) (Ser536) or β-actin was determined by immunoblotting with specific antibodies. The results are shown in FIG. 10C. Also, peritoneal macrophages were treated with LPS with or without 5-MTP (50 μM) for the indicated time. Phospho-p65 in the lysates was analyzed by an ELISA kit. The results are shown in FIG. 10D, in which the error bars denote mean ±SD (n=3). According to FIGS. 10C-10D, 5-MTP decreased LPS-induced phosphorylation of NF-κB p65 not only in RAW264.7 cells (FIG. 10C) but also in peritoneal macrophages (FIG. 10D).

Figure 10E:
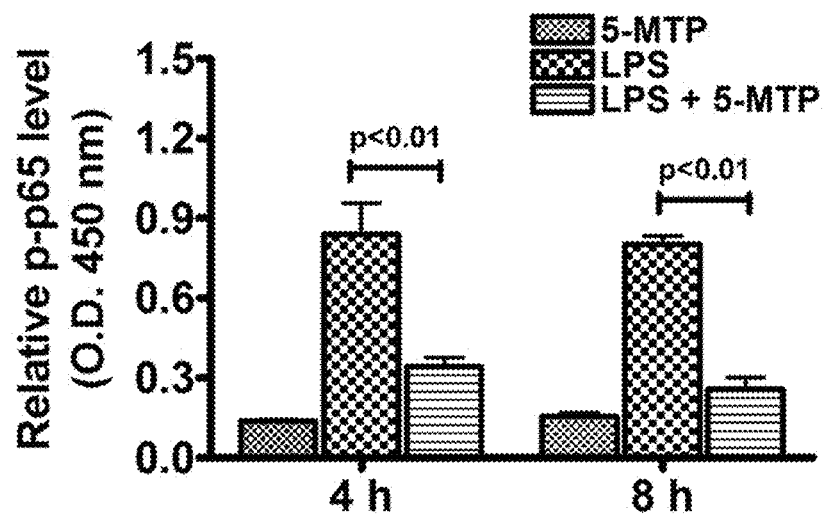
FIG. 10E shows phosphor-p65 level in lung tissues of mice after LPS infusion with or without 5-MTP.

Since NF-κB activation plays a critical role in the initiation and progression of systemic inflammation and septic pathology, the effect of 5-MTP on NF-κB activation in lung tissue was evaluated. Phospho-p65 level in lung tissues was determined by an ELISA kit at 4 and 8 h after LPS infusion with or without 5-MTP (23.4 mg/kg) (n=6 mice/group). The results shown in FIG. 10E indicate that LPS comparably increased the phosphorylation level of NF-κB p65 in lung tissues, which was reduced by 5-MTP.

5-MTP Suppresses p300 Histone Acetyltransferase (HAT) Activation.

Figure 10F:
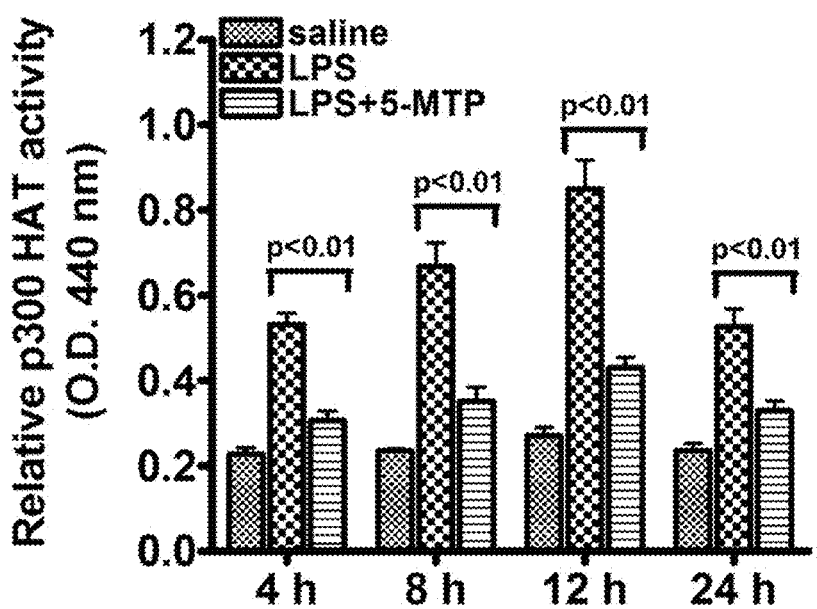
FIG. 10F shows p300 HAT activity in peritoneal macrophages treated with LPS in the presence or absence of 5-MTP.

Activation of p300 HAT plays an important role in transcriptional coactivation of NF-κB and expression of inflammatory genes, such as COX-2 and iNOS. Hence, we investigated the inhibition of 5-MTP on p300 HAT activation.

p300 HAT activity in peritoneal macrophages treated with LPS in the presence or absence of 5-MTP (50 μM) for the indicated time was measured with an p300 HAT activity assay kit. As shown in FIG. 10F, LPS activated p300 HAT in peritoneal macrophages at 4 h and persisted for 24 h. Also, 5-MTP significantly blocked p300 HAT activation up to 24 h.

Figure 10G:
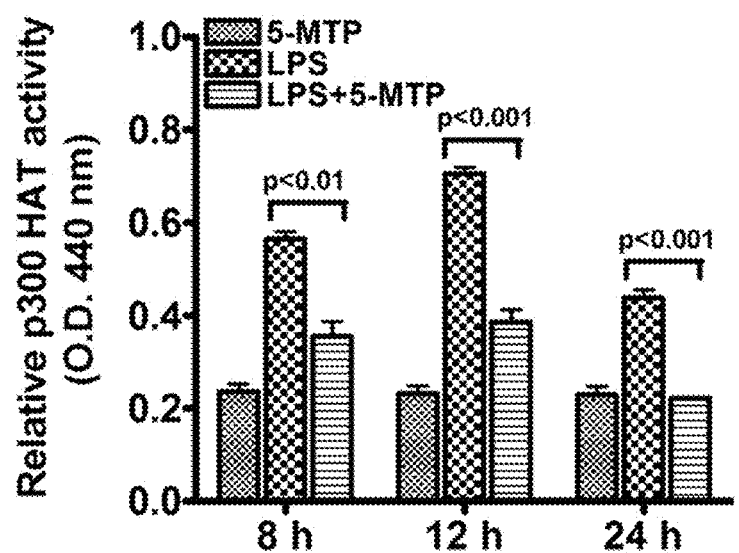
FIG. 10G shows p300 HAT activity in lung tissues of mice after LPS infusion with or without 5-MTP.

In addition, p300 HAT activity in lung tissues of mice (n=6 mice/group) at 8-24 h after LPS infusion with or without 5-MTP(23.4 mg/kg) was determined by an assay kit. As shown in FIG. 10G, in vivo, LPS elevated p300 HAT activity in lung tissues but was suppressed by 5-MTP as in macrophages in vitro.

Figure 10H:
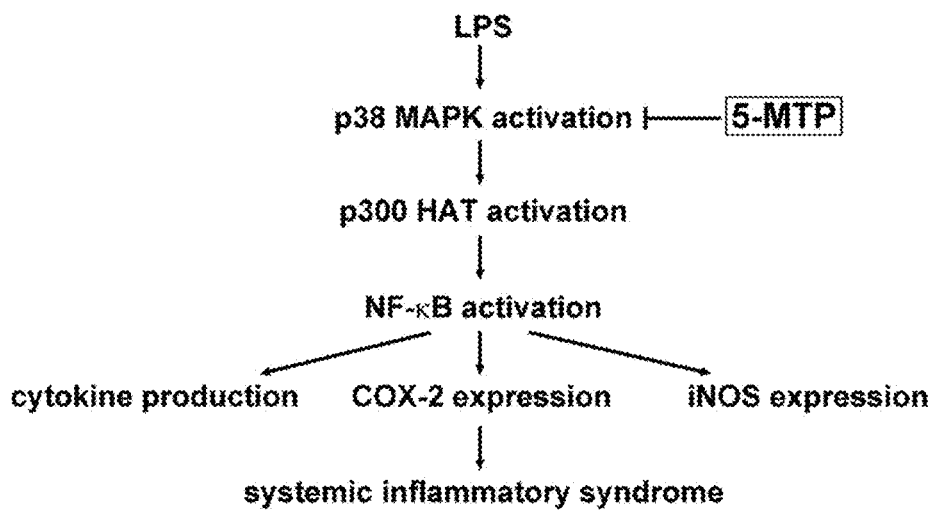
FIG. 10H shows schematic illustration of the signaling mechanisms via which 5-MTP inhibits systemic inflammatory syndrome.

Based on the results illustrated above, these results suggest that 5-MTP inhibits LPS-induced p300 HAT activation and NF-κB activity, thereby suppressing COX-2, iNOS and proinflammatory cytokine expressions. Collective inhibition of cytokines and proinflammatory COX-2 and iNOS accounts for the protective effect of 5-MTP on sepsis, which is represented in FIG. 10H.

Suppressive Effectiveness of 5-MTP, 5-MTPE and COX-2 Inhibitors and NF-κB Inhibitor in LPS-Induced COX-2 and IL-6 Expression.

Because COX-2 inhibitors are considered to be anti-inflammatory agent, we next evaluated the suppressive effectiveness of 5-MTP derivatives and COX-2 inhibitors, NS398 and SC560 in LPS-induced IL-6 production.

Herein, after pretreating RAW264.7 cells with different concentrations of 5-MTP, 5-MTPE, COX-2 inhibitors (NSC398 or SC560) and NF-κB inhibitor JSH-23 for 30 min, cells were also stimulated with LPS. In addition, RAW264.7 cells were also transfected with COX-2 promoter-luciferase plasmid. After 24 h transfection, the cells were incubated with LPS for 8 h. Luciferase activity as measured.

Figure 11A:
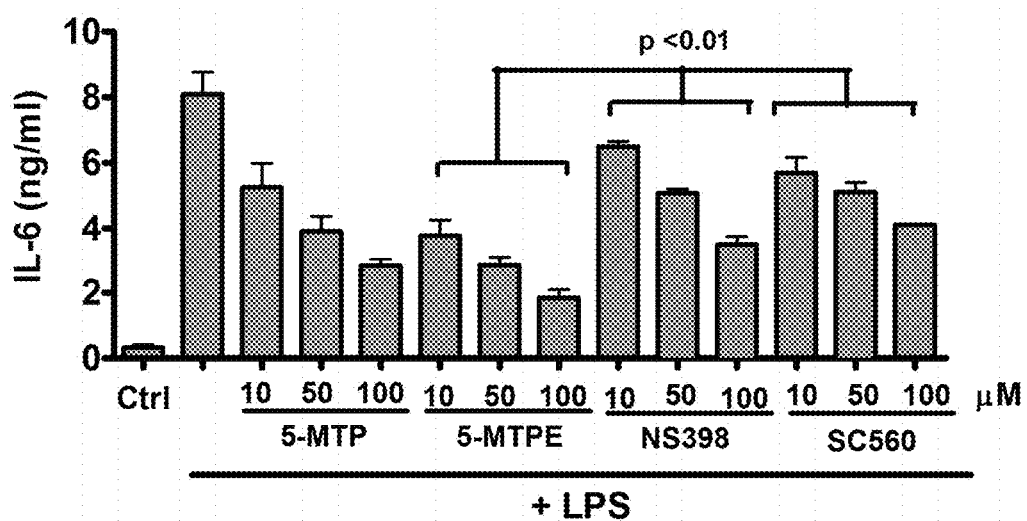
FIGS. 11A-11B shows IL-6 levels in culture supernatants of RAW264.7 cells treated with 5-MTP, 5-MTPE, COX-2 inhibitors (NSC398 or SC560) and NF-κB inhibitor JSH-23 after LPS treatment.

FIG. 11A shows IL-6 level in culture supernatants measured by ELISA at 24 h after LPS treatment. The results indicate that all used agents dose-dependably blocked LPS-induced IL-6 production in RAW264.7 cells. In comparison between each other, 5-MTPE possesses a better suppressive capacity on IL-6 production.

Figure 11B:
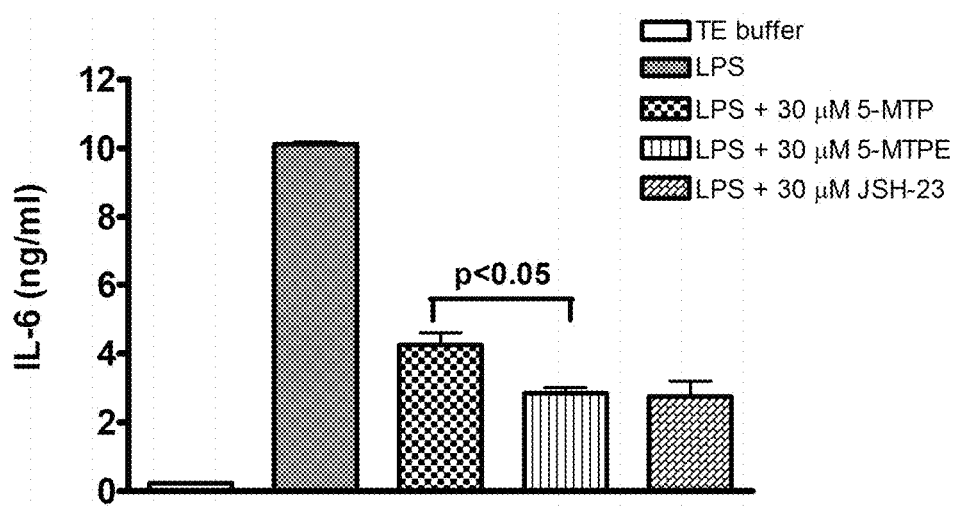
Figure 11C:
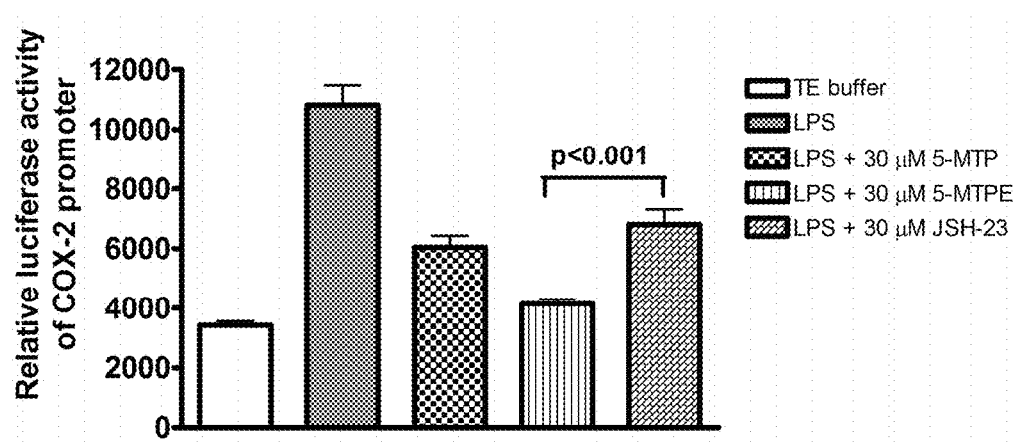
FIG. 11C shows luciferase activity after RAW264.7 cells were transfected with COX-2 promoter-luciferase plasmid.

As demonstrated above, 5-MTP inhibited LPS-induced systemic inflammation via suppressing NF-κB activation. Furthermore, NF-κB inhibitor has been reported to be anti-inflammatory and anti-cancer agent. We were to compare the suppressive effectiveness of 5-MTP derivatives with that of NF-κB inhibitor JSH-23 in LPS-induced COX-2 and IL-6 expression. As JSH-23 effect, both 5-MTP and 5MTPE dose-dependently blocked LPS-induced COX-2 and IL-6 production in RAW264.7 cells. Notably, the COX-2 and IL-6 suppressive activity of 5-MTPE is potent than that of NF-κB inhibitor JSH-23, as shown in FIG. 11B-11C.

Serum 5-MTP Concentrations Inversely Correlate with Coronary Artery Disease

Figure 12A:
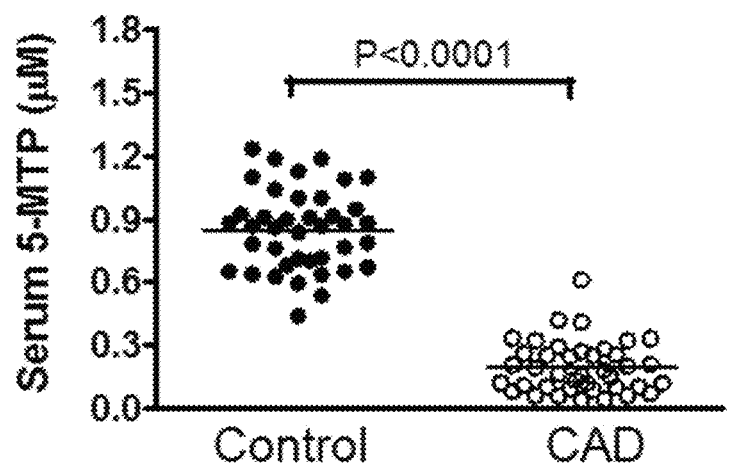
FIG. 12A shows serum 5-MTP concentrations in patients with coronary artery disease (CAD) (n=50) and healthy subjects (n=30) were measured by competitive 5-MTP ELISA.

To investigate the clinical relevance of 5-MTP in CAD, we measured serum 5-MTP levels in control subjects and patients with CAD. Forty control subjects (26 males and 14 females, mean age 50±11 years) and 40 CAD patients (31 males and 9 females, mean age 62±12 years) were included in the study. The presence of CAD was confirmed by coronary angiography and CAD was defined as more than 50% angiographic diameter stenosis in one or more coronary arteries. The body mass index was not different between control and CAD groups (25.5±3.7 vs. 25.6±4.1, respectively). Control subjects did not have any coronary vessel and known systemic disease. Serum was obtained from blood drawn from controls or patients prior to angiography. Measurements of 5-MTP with enzyme-immunoassays revealed that the mean serum 5-MTP levels from controls were 0.85±0.03 µmol/L (FIG. 12A). In contrast, serum 5-MTP concentrations of CAD patients were significantly reduced to 0.20±0.02 µmol/L (FIG. 12A, P<0.0001 vs. controls). These results indicate that serum 5-MTP concentrations inversely correlate with coronary artery disease.

Figure 12B:
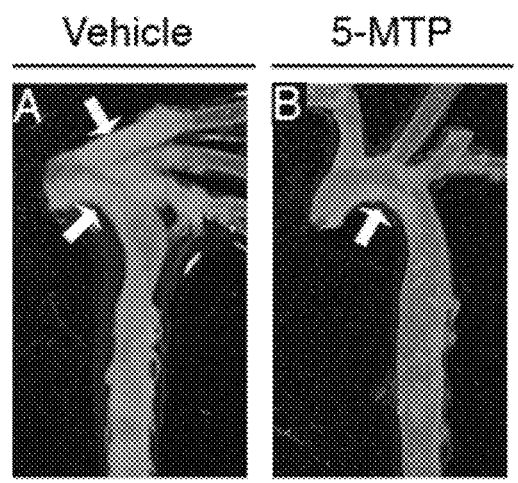
FIG. 12B shows inhibition of 5-MTP on lipid accumulation and atherosclerotic lesion formation in arteries of ApoE-deficient mice treat with high fat diet.
Figure 12C:
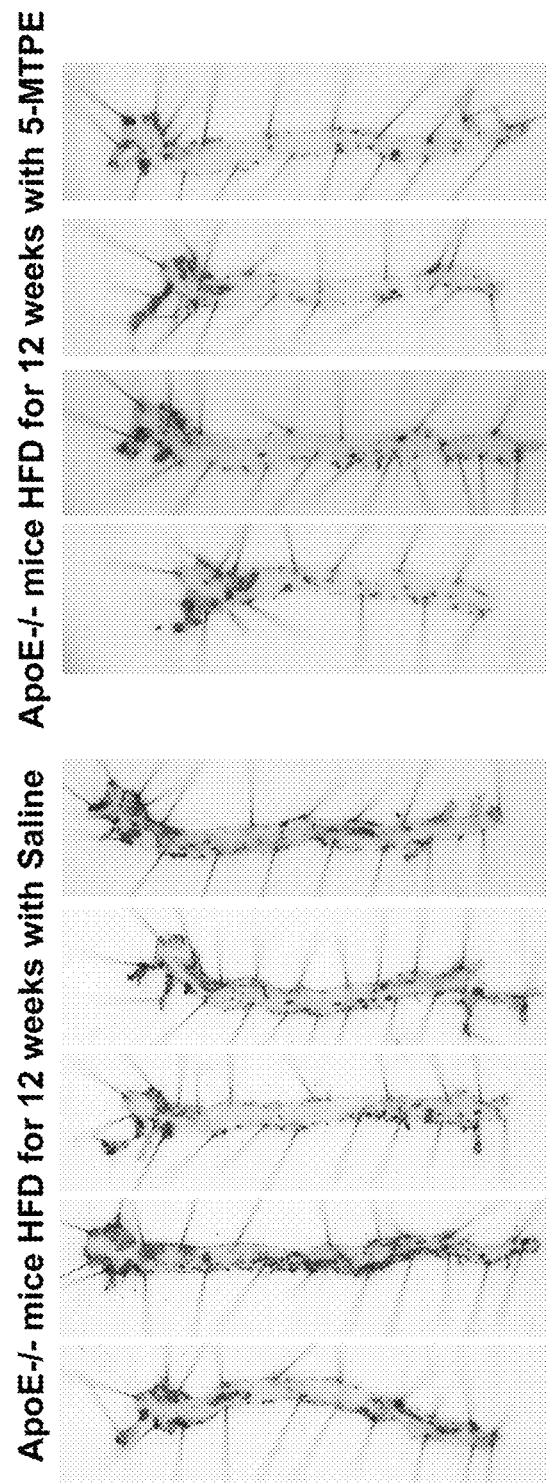
FIG. 12C shows inhibitions of 5-MTPE on lipid accumulation in atherosclerotic lesions of ApoE-deficient mice treat with high fat diet.

5-MTP Derivatives Protects Against Atherosclerosis and Vascular Calcification in ApoE-deficient Mice Since reduction of serum 5-MTP in CAD patients may be associated with the development of vascular disease, we determined whether exogenous 5-MTP derivatives exert protective effect in the development of atherosclerosis. ApoE-deficient mice were fed a Western high fat diet containing 1.25% cholesterol and 21% fat (Research Diets) starting at 6 weeks of age. The mice were simultaneously treated with vehicle (PBS), 5-MTP or 5-MTPE (23.5 mg/kg body weight, 3 times a week) by intraperitoneal injection. After 8 weeks, the aortic trees were dissected and lesions examined in the aortic arch and its branches. Our data from a pilot experiment indicated that the abundant whitish lipid accumulation was readily visible in vehicle-treated mice (FIG. 12B, arrows). In comparison, 5-MTP-treated mice had less lipid accumulation in the arteries (FIG. 12B, arrows). In similar results were observed in 5-MTPE-treated mice, Oil red O analysis indicated that 5-MTPE suppressed lipid accumulation in atherosclerotic lesions of ApoB-deficient mice treat with high fat diet as compared with vehicle-treated mice (FIG. 12C).

Figure 12D:
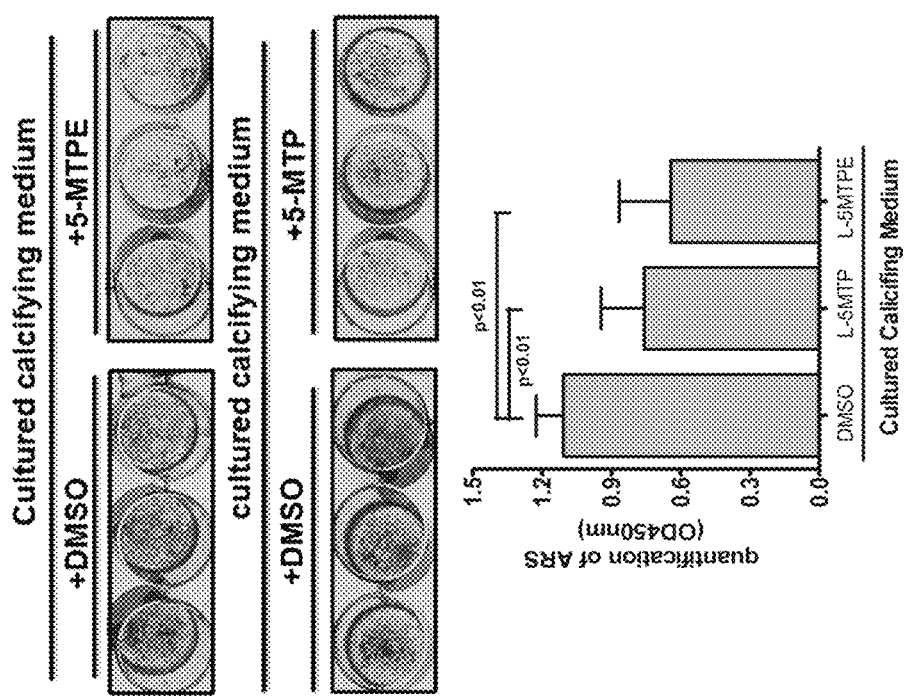
FIG. 12D shows suppressive effects of 5-MTP and 5-MTPE on calcifying medium-induced calcification in vascular smooth muscle cells.
Figure 12E:
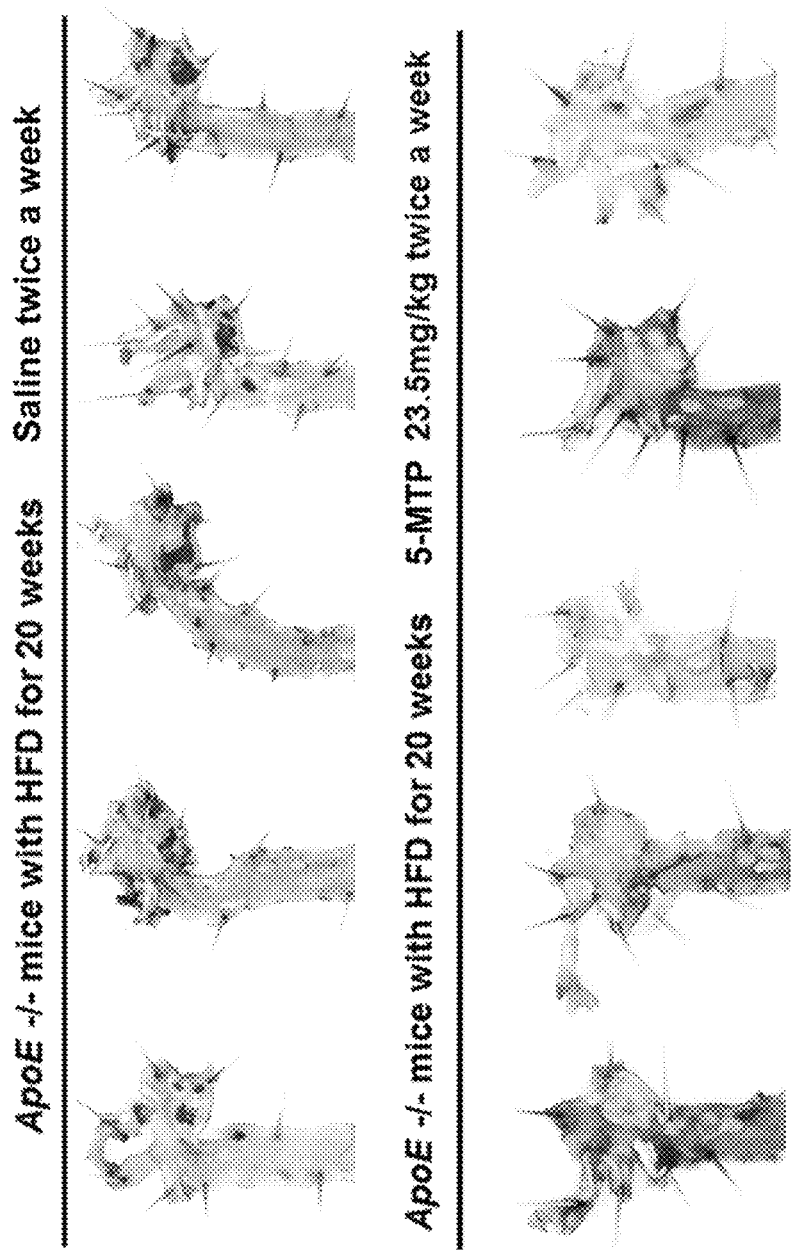
FIG. 12E shows inhibitions of 5-MTP on high fat diet-induced vascular calcification in ApoE-deficient mice.

Vascular smooth muscle cell (VSMC) calcification is the major phenomenon to induce atherosclerotic vascular calcification in cardiovascular disease (CVD). We next investigated the effect of 5-MTP derivatives on VSMC calcification. Calcifying medium-induced calcification in vascular smooth muscle cells was reduced by 5-MTP and 5-MTPE (FIG. 12D). In addition, 5-MTP also prevented high fat diet-induced vascular calcification in ApoE-deficient mice (FIG. 12E).

5-MTP Reduces Neointima Formation in a Mouse Carotid Artery Ligation Model

Figure 13:
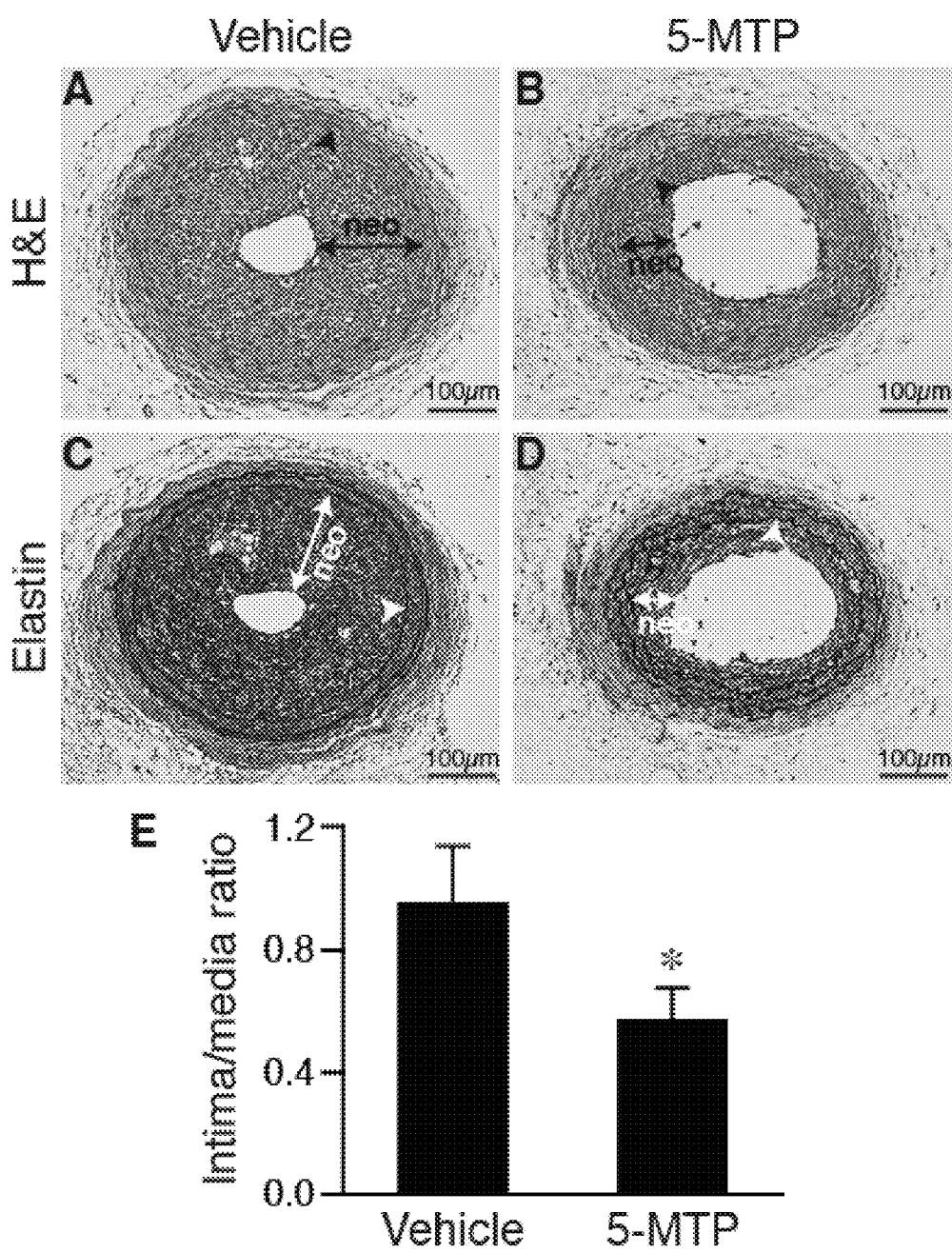
FIG. 13 shows attenuation of 5-MTP on intimal hyperplasia of the ligated mouse carotid arteries. Vessel sections were stained with H&E (A, B) or Verhoeff's staining for elastin (black) (C, D). (E) Quantitative morphometric analysis of intimal area in the ligated carotid arteries. Compared with vehicle-treated mice (0.96±0.19, n=9), 5-MTP reduced intima/media area ratio to 0.58±0.11 (n=12; *P<0.05 vs. vehicle group).

To begin to investigate the potential function of 5-MTP in vascular remodeling, we subjected mice to a neointima formation model of carotid artery ligation, and treated mice with vehicle or 5-MTP. Four weeks after ligation, H&E and elastin staining revealed robust neointima formation in vehicle-treated ligated carotid arteries (FIG. 13A, 13C). In contrast, intimal thickening was reduced in ligated carotids from 5-MTP-treated mice (FIG. 13B, 13D). Quantitative analysis showed that 5 MTP significantly decreased intima/media ratio from 0.96±0.19 of vehicle group (n=9) to 0.58±0.11 of 5-MTP group (n=12, P<0.05; FIG. 13E).

In conclusion, we have shown that 5-MTP and its derivatives, 5-MTPE and NACT-5-MTP are efficacious in controlling COX-2, cytokine and inflammatory mediator overproduction, accompanied by prevention of cancer cell growth and migration, lung damages and improvement of mortality caused by systemic inflammation. 5-MTP may exert its effects by functioning as a circulating hormone to control excessive COX-2 expression and systemic inflammation. 5-MTP and its derivatives will be a valuable drug and/or serves as a lead compound for developing new drugs for treating cancer and inflammatory diseases such as sepsis, Systemic Lupus Erythematosus (SLE), cardiovascular diseases, metabolic syndrome, cancer, septicemia and diverse inflammatory joint, gastrointestinal and renal diseases.

Although the present invention has been explained in relation to its preferred embodiment, it is to be understood that many other possible modifications and variations can be made without departing from the spirit and scope of the invention as hereinafter claimed.

What is claimed is:

1. A method for treating an inflammatory-related disease, comprising administering to a subject in need thereof and effective amount of a compound of formula (I):

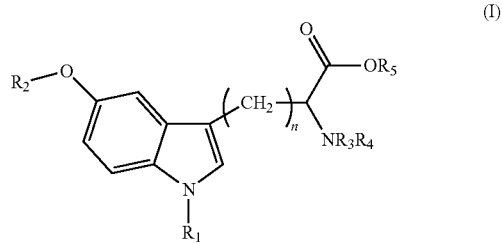

(I)

wherein the inflammatory-related disease is sepsis, cardiovascular diseases, or renal diseases; and, the compound is

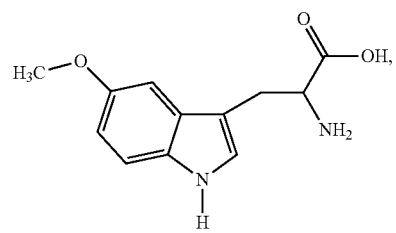

-continued
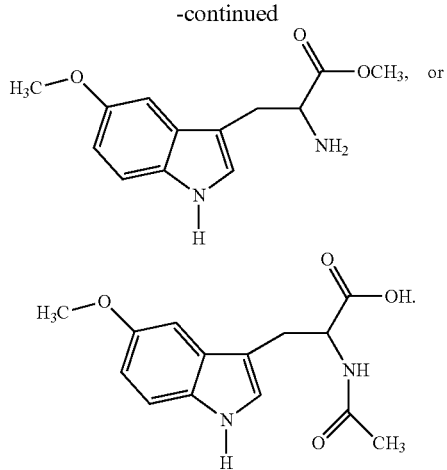
2. A method for treating a cancer, comprising administering to a subject in need thereof and effective amount of a compound of formula (I):
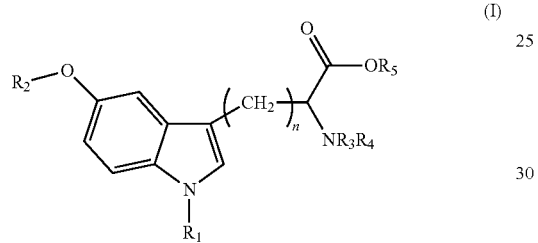
wherein the cancer is a lung cancer, or a breast cancer, and, the compound is
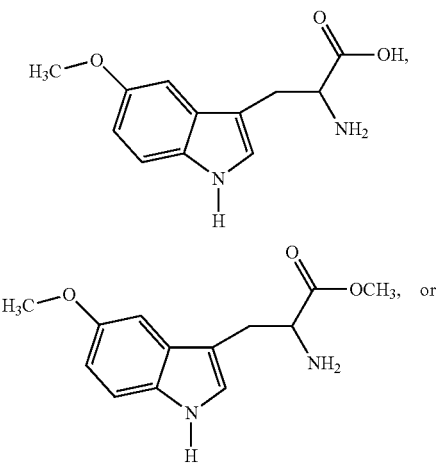
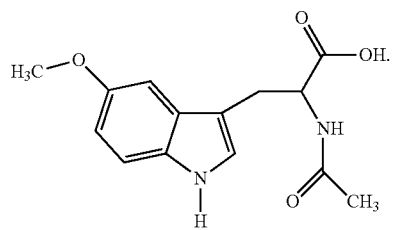
* * * * *